US011129812B2

(12) United States Patent
Feinbaum et al.

(10) Patent No.: US 11,129,812 B2
(45) Date of Patent: *Sep. 28, 2021

(54) OPHTHALMIC PHARMACEUTICAL COMPOSITIONS AND USES RELATING THERETO

(71) Applicant: ORASIS PHARMACEUTICALS LTD., Herzliya (IL)

(72) Inventors: Claes Feinbaum, Herzliya (IL); Franc Salamun, Nova Gorica (SI); Sudhir Patel, Stirling (GB)

(73) Assignee: ORASIS PHARMACEUTICALS LTD., Herzliya (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/831,535

(22) Filed: Mar. 26, 2020

(65) Prior Publication Data

US 2020/0222369 A1 Jul. 16, 2020

Related U.S. Application Data

(63) Continuation of application No. 16/032,044, filed on Jul. 10, 2018, now Pat. No. 10,639,297, which is a continuation of application No. 15/825,505, filed on Nov. 29, 2017, now abandoned, which is a continuation of application No. 15/680,967, filed on Aug. 18, 2017, now Pat. No. 9,867,810.

(60) Provisional application No. 62/377,154, filed on Aug. 19, 2016.

(51) Int. Cl.
| | | |
|---|---|---|
| A61K 31/4178 | (2006.01) | |
| A61K 9/00 | (2006.01) | |
| A61K 47/38 | (2006.01) | |
| A61K 47/36 | (2006.01) | |
| A61K 31/133 | (2006.01) | |
| A61K 31/196 | (2006.01) | |
| A61K 31/407 | (2006.01) | |
| A61K 31/728 | (2006.01) | |
| A61K 31/365 | (2006.01) | |

(52) U.S. Cl.
CPC ........ *A61K 31/4178* (2013.01); *A61K 9/0048* (2013.01); *A61K 31/133* (2013.01); *A61K 31/196* (2013.01); *A61K 31/365* (2013.01); *A61K 31/407* (2013.01); *A61K 31/728* (2013.01); *A61K 47/36* (2013.01); *A61K 47/38* (2013.01)

(58) Field of Classification Search
CPC .............. A61K 31/4178; A61K 9/0048; A61K 47/36; A61K 47/38
See application file for complete search history.

(56) References Cited

U.S. PATENT DOCUMENTS

| | | | |
|---|---|---|---|
| 4,255,415 A * | 3/1981 | Chrai | A61K 9/0048 424/606 |
| 5,422,116 A | 6/1995 | Yen et al. | |
| 5,698,533 A | 12/1997 | Kang | |
| 5,710,182 A | 1/1998 | Reunamaki et al. | |
| 5,759,532 A | 6/1998 | Galin et al. | |
| 5,795,913 A | 8/1998 | Lehmussaari et al. | |
| 5,948,401 A * | 9/1999 | Donabedian | A61K 9/0048 424/78.04 |
| 6,265,444 B1 | 7/2001 | Bowman et al. | |
| 6,273,092 B1 | 8/2001 | Nolan | |
| 6,383,471 B1 | 5/2002 | Chen et al. | |
| 6,410,544 B1 * | 6/2002 | Gwon | A61K 31/27 514/256 |
| 6,448,296 B2 | 9/2002 | Yasueda et al. | |
| 6,540,990 B2 | 4/2003 | Nolan | |
| 6,605,640 B2 | 8/2003 | Nolan | |
| 7,915,312 B2 | 3/2011 | Nolan | |
| 8,299,079 B2 | 10/2012 | Kaufman | |
| 8,524,758 B2 | 9/2013 | Benozzi | |
| 8,829,037 B2 | 9/2014 | Sharma | |
| 9,867,810 B1 | 1/2018 | Feinbaum et al. | |
| 9,987,254 B2 | 6/2018 | Hernandez et al. | |
| 10,639,297 B2 * | 5/2020 | Feinbaum | A61K 31/4178 |
| 2001/0029269 A1 | 10/2001 | Bowman et al. | |
| 2002/0035264 A1 | 3/2002 | Kararli et al. | |
| 2002/0128267 A1 | 9/2002 | Bandyopadhyay et al. | |
| 2002/0160988 A1 | 10/2002 | Amitai et al. | |
| 2003/0018382 A1 | 1/2003 | Pflugfelder et al. | |
| 2003/0124191 A1 | 7/2003 | Besse et al. | |
| 2004/0058926 A1 | 3/2004 | Bandyopadhyay et al. | |

(Continued)

FOREIGN PATENT DOCUMENTS

| | | | |
|---|---|---|---|
| EP | 0 216 453 B1 | 3/1996 | |
| EP | 0 507 224 B1 | 10/1996 | |

(Continued)

OTHER PUBLICATIONS

Atchison et al., "Subjective DoF of the eye," Optom Vis Sci. 1997, 74:511-520.
Atchison & Smith, "Optics of the human eye", Edinburgh UK, Buttersworths-Heinemann, 2000, Cover and p. 217.
Baffa et al., "Tear film and ocular surface alterations in chronic users of antiglaucoma medications," Arq Bras Oftalmol 2008, 71:18-21.
Barbee & Smith, "A comparative study of mydriatic and cycloplegic agents; in human subjects without eye disease," Am J Ophthalmol 1957, 44: 617-622.

(Continued)

*Primary Examiner* — James D. Anderson
(74) *Attorney, Agent, or Firm* — Finnegan, Henderson, Farabow, Garrett & Dunner LLP

(57) ABSTRACT

The disclosure relates to ophthalmic pharmaceutical compositions comprising pilocarpine or a pharmaceutically acceptable salt. Aspects of the disclosure further relate to uses and preparations of ophthalmic pharmaceutical compositions comprising pilocarpine or a pharmaceutically acceptable salt, for correcting presbyopia and other ocular conditions in a subject.

12 Claims, 2 Drawing Sheets

(56) References Cited

U.S. PATENT DOCUMENTS

| | | |
|---|---|---|
| 2005/0119262 A1 | 6/2005 | Wax |
| 2005/0208102 A1 | 9/2005 | Schultz |
| 2006/0002963 A1 | 1/2006 | Rabinovich-Guilatt et al. |
| 2008/0050335 A1 | 2/2008 | Faour et al. |
| 2008/0145430 A1 | 6/2008 | Panmai et al. |
| 2010/0016395 A1 | 1/2010 | Benozzi |
| 2010/0298335 A1 | 11/2010 | Kaufman |
| 2014/0024642 A1 | 1/2014 | Restrepo |
| 2014/0113946 A1 | 4/2014 | Abad |

FOREIGN PATENT DOCUMENTS

| | | |
|---|---|---|
| EP | 0 499 299 B1 | 8/2000 |
| EP | 0 197 718 B2 | 7/2001 |
| EP | 0 752 847 B1 | 7/2001 |
| EP | 0 995 435 B1 | 4/2007 |
| EP | 1938839 | 7/2008 |
| EP | 2 425 816 A2 | 3/2012 |
| JP | 1998500684 | 1/1998 |
| JP | 1999510497 | 9/1999 |
| JP | 2007500244 | 1/2007 |
| JP | 2010513454 | 4/2010 |
| JP | 2010528014 | 8/2010 |
| WO | WO 95/05163 | 2/1995 |
| WO | WO 95/31968 | 11/1995 |
| WO | WO 97/06782 | 2/1997 |
| WO | WO 97/33562 | 9/1997 |
| WO | WO 00/06135 | 2/2000 |
| WO | WO 01/95913 A1 | 12/2001 |
| WO | WO 02/100437 A2 | 12/2002 |
| WO | WO 2004112836 | 12/2004 |
| WO | WO 2005/062818 A2 | 7/2005 |
| WO | WO 2008/011836 A2 | 1/2008 |
| WO | WO 2008/130591 A2 | 10/2008 |
| WO | WO 2008153746 | 12/2008 |
| WO | WO 2011/079123 A1 | 6/2011 |
| WO | WO 2015/122853 A1 | 8/2015 |

OTHER PUBLICATIONS

Benard et al., "Optimizing the subjective depth-of-focus with combinations of fourth- and sixth-order spherical aberration," Vision Res 2011, 51:2471-2477.
Benozzi et al., "Presbyopia: a new potential pharmacological treatment." MEHDI Ophthalmology Journal 2012, 1(1): 3-5.
Birren et al., "Age changes in pupil size," J Gerontol 1950, 5:216-221.
Bucolo et al., "Pharmacological profile of a new topical pilocarpine formulation," Journal of Ocular Pharmacology and Therapeutics 1999, 15(6): 567-573.
Camber et al., "Influence of sodium hyaluronate on the meiotic effect of pilocarpine in rabbits," Current Eye Research 1987, 6(6):779-784.
Camber & Edman, "Sodium hyaluronate as an ophthalmic vehicle: some factors governing its effect on the ocular absorption of pilocarpine," Current Eye Research 1989, 8(6):563-567.
Charman, "Developments in the correction of presbyopia I: spectacle and contact lenses," Ophthalmic & Physiological Optics: the Journal of the College of Optometrists 2014, 34(1): 8-29.
Charman, "Developments in the correction of presbyopia II: surgical Approaches," Ophthalmic & Physiological Optics: the Journal of the College of Optometrists 2014, 34(4): 397-426.
Chrai et al., "Drop size and initial dosing frequency problems of topically applied ophthalmic drugs," Journal of Pharmaceutical Sciences 1974, 63(3):333-338.
Cleary et al., "Pilot study of new focus-shift accommodating intraocular lens," J Cataract Refract Surg 2010, 36:762-770.
Diestelhorst, "The additive intraocular pressure-lowering effect of latanoprost 0.005% daily once and pilocarpine 2% t.i.d. in patients with open-angle glaucoma or ocular hypertension," Graefes Arch Clin Exp Ophthalmol 2000, 238:433-439.
Edgar et al., "Effects of dipivefrin and pilocarpine on pupil diameter, automated perimetry and LogMAR acuity", Graefe's Arch Clin Exp Ophthalmol 1999, 237: 117-124.
Emsley, "Optics of Vision", 5th ed., Visual Optics vol. 1, London UK, Buttersworths, 1972, Cover and p. 88.
Frick et al., "The global burden of potential productivity loss from uncorrected presbyopia," Ophthalmology 2015, 122(8): 1706-1710.
Gil-Cazorla et al., "A review of the surgical options for the correction of presbyopia," British Journal of Ophthalmology 2016, 100(1): 62-70.
Goertz et al., "Review of the impact of presbyopia on quality of life in the developing and developed world," Ophthalmologica 2014, 92(6): 497-500.
Gupta et al., "Is randomisation necessary for measuring defocus curves in pre-presbyopes?" Cont Lenses Anterior Eye 2007, 30:119-124.
Harris & Galin, "Effect of ocular pigmentation on hypotensive response to pilocarpine," Am J Ophthalmol 1971, 72:923-925.
Havener, WH Ocular Pharmacology 2nd ed. CV Mosby & Co, USA, 1970, Cover, pp. 207-209, 213, 219, 223, and 243.
Holden et al., "Global vision impairment due to uncorrected presbyopia," 2008 126(12): 1731-1739.
Hoffman et al., "Cataract surgery and nonsteroidal antiinflammatory drugs," Cataract Refract Surg 2016, 42: 1368-1379.
ISOPTO® Carpine Product Label, Alcon Laboratories, Inc., 2010, 5 pages.
Jain et al., "Newer trends in insitu gelling systems for controlled ocular drug delivery," Journal of Analytical & Pharmaceutical Research, 2016, 2(3): 1-16.
Kamlesh & Kaushik, "Contrast sensitivity and depth of focus with aspheric multifocal versus conventional monofocal intraocular lens," Can J Ophthalmol 2001, 36:197-201.
Marcos et al., "The depth-of-field of the human eye from objective and subjective measurements," Vision Research 1999, 39: 2039-2049.
Macsai et al., "Visual outcomes after accommodating intraocular lens implantation," J Cataract Refract Surg 2006, 32:628-633.
Mazor et al., "Piloplex, a new long-acting pilocarpine polymer salt, B: Comparative study of the visual effects of pilocarpine and Piloplex eye drops," British Journal of Ophthalmology, 1979, 63: 48-51.
Mordi & Ciufredda, "Static aspects of accommodation: age and presbyopia," Vision Res. 1998, 38:1643-1653.
Nishi et al., "Comparisons of amplitude of pseudoaccommodation with aspheric yellow, spheric yellow, and spheric clear monofocal intraocular lenses," Clin Ophthalmol 2013, 7:2159-2164.
Nordmann et al., "Comparison of the intraocular pressure lowering eVect of latanoprost and a fixed combination of timolol-pilocarpine eye drops in patients insuYciently controlled with â adrenergic antagonists," Br J Ophthalmol 2000, 84:181-185.
Nuzzi et al., "Adverse effects of topical antiqlaucomatous medications on the conjunctiva and the lachrymal (Brit. Engl) response," Int Ophthalmol 1998, 22:31-35.
Pallikaris et al., "Real and pseudoaccommodation in accommodative lenses," J Ophthalmol 2011, 284961, doi: 10.1155/2011/284961.
Patel et al., "Presbyopia: prevalence, impact, and interventions," Community eye health / International Centre for Eye Health 2007, 20(63): 40-41.
Ronchi & Moleskini, "Depth of focus in peripheral vision," Ophthalmic Res 1975, 7:152-157.
Sergienko & Tutchenko, "Depth of focus: clinical manifestation," Eur J Ophthalmol 2007, 17:836-840.
Smith et al., "An increased effect of pilocarpine on the pupil by application of the drug in oil," Brit J Ophthalmol 1978, 62:314-317.
Tabanero & Artal, "Optical modeling of a corneal inlay in real eyes to increase depth of focus: Optimum centration and residual defocus," J Cataract Refract Surg 2012, 38:270-277.
Toto et al., "Visual performance and biocompatibility of 2 multifocal diffractive IOLs," J Cataract Refract Surg 2007, 33:1419-1425.
Voltaren Ophthalmics® Product Label, Novartis, 2012, 5 pages.
Wang & Ciufredda, Depth-of-focus of the human eye: theory and clinical implications, Surv Ophthalmol 2006, 51:75-85.

(56) References Cited

OTHER PUBLICATIONS

Williams, "Accommodative blur in pilocarpine-treated glaucoma," J Am Optom Assoc 1976, 47:761-764.
Winn et al., "Factors affecting light-adapted pupil size in normal human subjects," Investigative Ophthalmology & Visual Science 1994, 35:1132-1137.
Yao et al., "Objective depth-of-focus is different from subjective depth-of-focus and correlated with accommodative microfluctuations," Vision Res 2010, 50:1266-1273.
Zimmer & Wheeler, "Miotics side effects and ways to avoid them," Ophthalmology 1982, 89:76-80.
Shen et al., "Inhibition of diclofenac forumulated in hyaluronan on angiogenesis in vitro and its intraocular tolerance in the rabbit eye", Graefe's Arch Clin Exp Ophthalmol 2000, 238:272-282.
Japanese Office Action of Application No. 2019-508247 dated Apr. 27, 2021.

\* cited by examiner

OPHTHALMIC PHARMACEUTICAL COMPOSITIONS AND USES RELATING THERETO

CROSS-REFERENCE TO RELATED APPLICATIONS

This application is a continuation of U.S. patent application Ser. No. 16/032,044, filed Jul. 10, 2018; which is a continuation of U.S. patent application Ser. No. 15/825,505, filed Nov. 29, 2017; which is a continuation of U.S. patent application Ser. No. 15/680,967, filed Aug. 18, 2017 (now U.S. Pat. No. 9,867,810, issued Jan. 16, 2018), which claims the benefit of U.S. Provisional Application No. 62/377,154, filed Aug. 19, 2016. The entire contents of each of these applications are incorporated herein by reference.

FIELD

The disclosure relates to ophthalmic pharmaceutical compositions comprising pilocarpine or a pharmaceutically acceptable salt thereof. Aspects of the disclosure further relate to preparations and uses of ophthalmic pharmaceutical compositions comprising pilocarpine or a pharmaceutically acceptable salt, for correcting presbyopia and other ocular conditions in a subject.

BACKGROUND

Presbyopia is an impairment of near vision that results from a gradual loss of lens accommodation usually after the age of 40 to 45 years. It is the most common physiological change occurring in the adult eye and may significantly affect quality of life and productivity when uncorrected (Frick et al., 2015, Ophthalmology 122(8): 1706-1710; Goertz et al., 2014, Acta Ophthalmologica 92(6): 497-500; Patel et al., 2007, Community eye health/International Centre for Eye Health 20(63): 40-41). The main symptom of this condition is a progressive blurring of vision when performing near tasks (reading, sewing, working at a computer etc.). This can occur in the absence of any visual symptoms associated with distance vision. It is estimated that global prevalence of presbyopia will be 1.4 billion individuals by 2020 (Holden et al., 2008, Archives of Ophthalmology 126(12): 1731-1739).

Methods for correcting presbyopia may involve both fixed and variable-focus lens systems (spectacles or contact lenses with monofocal, bifocal or multifocal design), and surgical procedures which modify the optics of the cornea, replace the crystalline lens with different fixed optics, or attempt to at least partially restore active accommodation (Charman, 2014, Ophthalmic & Physiological Optics: the Journal of the College of Optometrists 34(1): 8-29, Charman, 2014, Ophthalmic & Physiological Optics: the Journal of the College of Optometrists 34(4): 397-426; Gil-Cazorla et al., 2016, British Journal of Ophthalmology 100(1): 62-70). However, corrective lens systems may be cumbersome or provide inadequate treatment, while surgical methods can be invasive and are not without risks. For example, a patient may have trouble with night vision after the surgical intervention. Currently, no clinically effective pharmaceutical preparations are available to treat the symptoms of presbyopia.

Accordingly, to avoid the clear disadvantages for patients who are forced to wear corrective lenses or to undergo undesired surgeries with risks, there remains a need for new ways of ameliorating or correcting presbyopia.

SUMMARY

The disclosure relates to ophthalmic pharmaceutical compositions comprising pilocarpine or a pharmaceutically acceptable salt thereof. The disclosure also provides for preparations (e.g., kit or implant) comprising ophthalmic pharmaceutical compositions comprising pilocarpine or a pharmaceutically acceptable salt thereof. Aspects of the disclosure further provide for methods useful for correcting presbyopia and other ocular conditions in a subject.

Certain embodiments of the present disclosure are summarized in the following paragraphs. This list is only exemplary and not exhaustive of all of the embodiments provided by this disclosure.

Embodiment 1. An ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 2. The ophthalmic pharmaceutical composition of embodiment 1, wherein the pilocarpine salt is pilocarpine hydrochloride or pilocarpine nitrate.

Embodiment 3. The ophthalmic pharmaceutical composition of embodiment 1, wherein the ophthalmic pharmaceutical composition further comprises diclofenac or a pharmaceutically acceptable salt thereof at a concentration of 0.001% (w/w or w/v) to 0.090% (w/w or w/v), or ketorolac or a pharmaceutically acceptable salt thereof at a concentration of 0.01% (w/w or w/v) to 0.60% (w/w or w/v).

Embodiment 4. The ophthalmic pharmaceutical composition of embodiment 3, wherein the diclofenac salt is diclofenac sodium, or wherein the ketorolac salt is ketorolac tromethamine.

Embodiment 5. The ophthalmic pharmaceutical composition of embodiment 1, wherein the ophthalmic pharmaceutical composition further comprises a lubricating agent.

Embodiment 6. The ophthalmic pharmaceutical composition of embodiment 5, wherein the lubricating agent is hyaluronic acid or a pharmaceutically acceptable salt thereof, cellulose or its derivative, carboxymethyl cellulose sodium, hydroxyethyl cellulose, hydroxypropyl methylcellulose, methylcellulose, dextran, gelatin, a polyol, glycerin, polyethylene glycol 300, polyethylene glycol 400, polysorbate, propylene glycol, polyvinyl alcohol, povidone, or mixtures thereof.

Embodiment 7. The ophthalmic pharmaceutical composition of embodiment 6, wherein the lubricating agent is sodium hyaluronate, or hydroxypropyl methylcellulose, or mixtures thereof.

Embodiment 8. The ophthalmic pharmaceutical composition of embodiment 7, wherein the sodium hyaluronate is present at a concentration of 0.01% (w/w or w/v) to 0.9% (w/w or w/v), and/or wherein the hydroxypropyl methylcellulose is present at a concentration of 0.1% (w/w or w/v) to 2.0% (w/w or w/v).

Embodiment 9. The ophthalmic pharmaceutical composition of embodiment 1, wherein the ophthalmic pharmaceutical composition comprises:

(1) pilocarpine hydrochloride or pilocarpine nitrate at a concentration of 0.01% (w/w or w/v) to 0.4% (w/w or w/v), diclofenac sodium at a concentration of 0.001% (w/w or w/v) to 0.090% (w/w or w/v), and sodium hyaluronate at a concentration of 0.01% (w/w or w/v) to 0.9% (w/w or w/v);

(2) pilocarpine hydrochloride or pilocarpine nitrate at a concentration of 0.01% (w/w or w/v) to 0.4% (w/w or w/v), diclofenac sodium at a concentration of 0.001% (w/w or w/v) to 0.090% (w/w or w/v), and hydroxypropyl methylcellulose at a concentration of 0.1% (w/w or w/v) to 2.0% (w/w or w/v);

(3) pilocarpine hydrochloride or pilocarpine nitrate at a concentration of 0.01% (w/w or w/v) to 0.4% (w/w or w/v), ketorolac tromethamine at a concentration of 0.01% (w/w or w/v) to 0.60% (w/w or w/v), and sodium hyaluronate at a concentration of 0.01% (w/w or w/v) to 0.9% (w/w or w/v);

(4) pilocarpine hydrochloride or pilocarpine nitrate at a concentration of 0.01% (w/w or w/v) to 0.4% (w/w or w/v), ketorolac tromethamine at a concentration of 0.01% (w/w or w/v) to 0.60% (w/w or w/v), and hydroxypropyl methylcellulose at a concentration of 0.1% (w/w or w/v) to 2.0% (w/w or w/v); or (5) pilocarpine hydrochloride or pilocarpine nitrate at a concentration of 0.01% (w/w or w/v) to 0.4% (w/w or w/v), diclofenac sodium at a concentration of 0.001% (w/w or w/v) to 0.090% (w/w or w/v), sodium hyaluronate at a concentration of 0.01% (w/w or w/v) to 0.9% (w/w or w/v), and hydroxypropyl methylcellulose at a concentration of 0.1% (w/w or w/v) to 2.0% (w/w or w/v).

Embodiment 10. The ophthalmic pharmaceutical composition of embodiment 1, wherein the ophthalmic pharmaceutical composition is selected from compositions 1-32, and wherein each of compositions 1-32 comprises pilocarpine hydrochloride or pilocarpine nitrate, diclofenac sodium, and sodium hyaluronate as follows:

| Composition | pilocarpine hydrochloride or pilocarpine nitrate (w/w or w/v) | diclofenac sodium (w/w or w/v) | sodium hyaluronate (w/w or w/v) |
|---|---|---|---|
| 1 | 0.1% | 0% | 0% |
| 2 | 0.1% | 0.001% | 0% |
| 3 | 0.1% | 0.006% | 0% |
| 4 | 0.1% | 0.090% | 0% |
| 5 | 0.1% | 0% | 0.01% |
| 6 | 0.1% | 0% | 0.1% |
| 7 | 0.1% | 0% | 0.9% |
| 8 | 0.1% | 0.001% | 0.01% |
| 9 | 0.1% | 0.001% | 0.1% |
| 10 | 0.1% | 0.001% | 0.9% |
| 11 | 0.1% | 0.006% | 0.01% |
| 12 | 0.1% | 0.006% | 0.1% |
| 13 | 0.1% | 0.006% | 0.9% |
| 14 | 0.1% | 0.090% | 0.01% |
| 15 | 0.1% | 0.090% | 0.1% |
| 16 | 0.1% | 0.090% | 0.9% |
| 17 | 0.2% | 0% | 0% |
| 18 | 0.2% | 0.001% | 0% |
| 19 | 0.2% | 0.006% | 0% |
| 20 | 0.2% | 0.090% | 0% |
| 21 | 0.2% | 0% | 0.01% |
| 22 | 0.2% | 0% | 0.1% |
| 23 | 0.2% | 0% | 0.9% |
| 24 | 0.2% | 0.001% | 0.01% |
| 25 | 0.2% | 0.001% | 0.1% |
| 26 | 0.2% | 0.001% | 0.9% |
| 27 | 0.2% | 0.006% | 0.01% |
| 28 | 0.2% | 0.006% | 0.1% |
| 29 | 0.2% | 0.006% | 0.9% |
| 30 | 0.2% | 0.090% | 0.01% |
| 31 | 0.2% | 0.090% | 0.1% |
| 32 | 0.2% | 0.090% | 0.9% |

Embodiment 11. The ophthalmic pharmaceutical composition of embodiment 1, wherein the ophthalmic pharmaceutical composition is selected from compositions 33-64, and wherein each of compositions 33-64 comprises pilocarpine hydrochloride or pilocarpine nitrate, diclofenac sodium, and hydroxypropyl methylcellulose as follows:

| Composition | pilocarpine hydrochloride or pilocarpine nitrate (w/w or w/v) | diclofenac sodium (w/w or w/v) | hydroxypropyl methylcellulose (w/w or w/v) |
|---|---|---|---|
| 33 | 0.1% | 0% | 0% |
| 34 | 0.1% | 0.001% | 0% |
| 35 | 0.1% | 0.006% | 0% |
| 36 | 0.1% | 0.090% | 0% |
| 37 | 0.1% | 0% | 0.1% |
| 38 | 0.1% | 0% | 0.8% |
| 39 | 0.1% | 0% | 1.2% |
| 40 | 0.1% | 0.001% | 0.1% |
| 41 | 0.1% | 0.001% | 0.8% |
| 42 | 0.1% | 0.001% | 1.2% |
| 43 | 0.1% | 0.006% | 0.1% |
| 44 | 0.1% | 0.006% | 0.8% |
| 45 | 0.1% | 0.006% | 1.2% |
| 46 | 0.1% | 0.090% | 0.1% |
| 47 | 0.1% | 0.090% | 0.8% |
| 48 | 0.1% | 0.090% | 1.2% |
| 49 | 0.2% | 0% | 0% |
| 50 | 0.2% | 0.001% | 0% |
| 51 | 0.2% | 0.006% | 0% |
| 52 | 0.2% | 0.090% | 0% |
| 53 | 0.2% | 0% | 0.1% |
| 54 | 0.2% | 0% | 0.8% |
| 55 | 0.2% | 0% | 1.2% |
| 56 | 0.2% | 0.001% | 0.1% |
| 57 | 0.2% | 0.001% | 0.8% |
| 58 | 0.2% | 0.001% | 1.2% |
| 59 | 0.2% | 0.006% | 0.1% |
| 60 | 0.2% | 0.006% | 0.8% |
| 61 | 0.2% | 0.006% | 1.2% |
| 62 | 0.2% | 0.090% | 0.1% |
| 63 | 0.2% | 0.090% | 0.8% |
| 64 | 0.2% | 0.090% | 1.2% |

Embodiment 12. The ophthalmic pharmaceutical composition of embodiment 1, wherein the ophthalmic pharmaceutical composition is selected from compositions 65-96, and wherein each of compositions 65-96 comprises pilocarpine hydrochloride or pilocarpine nitrate, ketorolac tromethamine, and sodium hyaluronate as follows:

| Composition | pilocarpine hydrochloride or pilocarpine nitrate (w/w or w/v) | ketorolac tromethamine (w/w or w/v) | sodium hyaluronate (w/w or w/v) |
|---|---|---|---|
| 65 | 0.1% | 0% | 0% |
| 66 | 0.1% | 0.01% | 0% |
| 67 | 0.1% | 0.30% | 0% |
| 68 | 0.1% | 0.50% | 0% |
| 69 | 0.1% | 0% | 0.01% |
| 70 | 0.1% | 0% | 0.1% |
| 71 | 0.1% | 0% | 0.9% |
| 72 | 0.1% | 0.01% | 0.01% |
| 73 | 0.1% | 0.01% | 0.1% |
| 74 | 0.1% | 0.01% | 0.9% |
| 75 | 0.1% | 0.30% | 0.01% |
| 76 | 0.1% | 0.30% | 0.1% |
| 77 | 0.1% | 0.30% | 0.9% |
| 78 | 0.1% | 0.50% | 0.01% |
| 79 | 0.1% | 0.50% | 0.1% |
| 80 | 0.1% | 0.50% | 0.9% |
| 81 | 0.2% | 0% | 0% |
| 82 | 0.2% | 0.01% | 0% |
| 83 | 0.2% | 0.30% | 0% |
| 84 | 0.2% | 0.50% | 0% |
| 85 | 0.2% | 0% | 0.01% |
| 86 | 0.2% | 0% | 0.1% |
| 87 | 0.2% | 0% | 0.9% |
| 88 | 0.2% | 0.01% | 0.01% |
| 89 | 0.2% | 0.01% | 0.1% |
| 90 | 0.2% | 0.01% | 0.9% |
| 91 | 0.2% | 0.30% | 0.01% |

-continued

| Composition | pilocarpine hydrochloride or pilocarpine nitrate (w/w or w/v) | ketorolac tromethamine (w/w or w/v) | sodium hyaluronate (w/w or w/v) |
|---|---|---|---|
| 92 | 0.2% | 0.30% | 0.1% |
| 93 | 0.2% | 0.30% | 0.9% |
| 94 | 0.2% | 0.50% | 0.01% |
| 95 | 0.2% | 0.50% | 0.1% |
| 96 | 0.2% | 0.50% | 0.9% |

Embodiment 13. The ophthalmic pharmaceutical composition of embodiment 1, wherein the ophthalmic pharmaceutical composition is selected from compositions 97-128, and wherein each of compositions 97-128 comprises pilocarpine hydrochloride or pilocarpine nitrate, ketorolac tromethamine, and hydroxypropyl methylcellulose as follows:

| Composition | pilocarpine hydrochloride or pilocarpine nitrate (w/w or w/v) | ketorolac tromethamine (w/w or w/v) | hydroxypropyl methylcellulose (w/w or w/v) |
|---|---|---|---|
| 97 | 0.1% | 0% | 0% |
| 98 | 0.1% | 0.01% | 0% |
| 99 | 0.1% | 0.30% | 0% |
| 100 | 0.1% | 0.50% | 0% |
| 101 | 0.1% | 0% | 0.1% |
| 102 | 0.1% | 0% | 0.8% |
| 103 | 0.1% | 0% | 1.2% |
| 104 | 0.1% | 0.01% | 0.1% |
| 105 | 0.1% | 0.01% | 0.8% |
| 106 | 0.1% | 0.01% | 1.2% |
| 107 | 0.1% | 0.30% | 0.1% |
| 108 | 0.1% | 0.30% | 0.8% |
| 109 | 0.1% | 0.30% | 1.2% |
| 110 | 0.1% | 0.50% | 0.1% |
| 111 | 0.1% | 0.50% | 0.8% |
| 112 | 0.1% | 0.50% | 1.2% |
| 113 | 0.2% | 0% | 0% |
| 114 | 0.2% | 0.01% | 0% |
| 115 | 0.2% | 0.30% | 0% |
| 116 | 0.2% | 0.50% | 0% |
| 117 | 0.2% | 0% | 0.1% |
| 118 | 0.2% | 0% | 0.8% |
| 119 | 0.2% | 0% | 1.2% |
| 120 | 0.2% | 0.01% | 0.1% |
| 121 | 0.2% | 0.01% | 0.8% |
| 122 | 0.2% | 0.01% | 1.2% |
| 123 | 0.2% | 0.30% | 0.1% |
| 124 | 0.2% | 0.30% | 0.8% |
| 125 | 0.2% | 0.30% | 1.2% |
| 126 | 0.2% | 0.50% | 0.1% |
| 127 | 0.2% | 0.50% | 0.8% |
| 128 | 0.2% | 0.50% | 1.2% |

Embodiment 14. The ophthalmic pharmaceutical composition of embodiment 1, wherein the ophthalmic pharmaceutical composition is a slow release composition.

Embodiment 15. The ophthalmic pharmaceutical composition of embodiment 1, wherein the ophthalmic pharmaceutical composition is in the form of a suspension, gel, ointment, injectable solution, spray, or eye drop formulation.

Embodiment 16. The ophthalmic pharmaceutical composition of embodiment 1, wherein the ophthalmic pharmaceutical composition is suitable for implantation in or on a subject's eye or tissue surrounding the eye.

Embodiment 17. The ophthalmic pharmaceutical composition of embodiment 16, wherein the ophthalmic pharmaceutical composition is suitable for implantation into subconjunctival space, naso-lacrimal duct, or vitreous body of the subject.

Embodiment 18. The ophthalmic pharmaceutical composition of embodiment 1, wherein the ophthalmic pharmaceutical composition is suitable for topical delivery to a subject's eye or tissue surrounding the eye.

Embodiment 19. The ophthalmic pharmaceutical composition of embodiment 1, wherein the ophthalmic pharmaceutical composition comprises a pharmaceutically acceptable diluent, preservative, and/or solvent.

Embodiment 20. The ophthalmic pharmaceutical composition of embodiment 1, further comprising an isotonic agent, a wetting agent, a buffer, a stabilizer, a pH agent, a solubilizer, a thickening agent, and/or a dispersing agent.

Embodiment 21. The ophthalmic pharmaceutical composition of embodiment 1, wherein the ophthalmic pharmaceutical composition is effective for correction of presbyopia for up to 24 hours.

Embodiment 22. The ophthalmic pharmaceutical composition of embodiment 1, wherein the ophthalmic pharmaceutical composition corrects presbyopia without adversely affecting night vision.

Embodiment 23. The ophthalmic pharmaceutical composition of embodiment 1, wherein the ophthalmic pharmaceutical composition corrects presbyopia without adversely reducing visual field.

Embodiment 24. A method of correcting presbyopia in a subject comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 25. The method of embodiment 24, wherein the pilocarpine salt is pilocarpine hydrochloride or pilocarpine nitrate.

Embodiment 26. The method of embodiment 24, wherein the ophthalmic pharmaceutical composition further comprises diclofenac or a pharmaceutically acceptable salt thereof at a concentration of 0.001% (w/w or w/v) to 0.090% (w/w or w/v), or ketorolac or a pharmaceutically acceptable salt thereof at a concentration of 0.01% (w/w or w/v) to 0.60% (w/w or w/v).

Embodiment 27. The method of embodiment 26, wherein the diclofenac salt is diclofenac sodium, or wherein the ketorolac salt is ketorolac tromethamine.

Embodiment 28. The method of embodiment 24, wherein the ophthalmic pharmaceutical composition further comprises a lubricating agent.

Embodiment 29. The method of embodiment 28, wherein the lubricating agent is hyaluronic acid or a pharmaceutically acceptable salt thereof, cellulose or its derivative, carboxymethyl cellulose sodium, hydroxyethyl cellulose, hydroxypropyl methylcellulose, methylcellulose, dextran, gelatin, a polyol, glycerin, polyethylene glycol 300, polyethylene glycol 400, polysorbate, propylene glycol, polyvinyl alcohol, povidone, or mixtures thereof.

Embodiment 30. The method of embodiment 29, wherein the lubricating agent is sodium hyaluronate, or hydroxypropyl methylcellulose, or mixtures thereof.

Embodiment 31. The method of embodiment 30, wherein the sodium hyaluronate is present at a concentration of 0.01% (w/w or w/v) to 0.9% (w/w or w/v), and/or wherein the hydroxypropyl methylcellulose is present at a concentration of 0.1% (w/w or w/v) to 2.0% (w/w or w/v).

Embodiment 32. The method of embodiment 24, wherein the ophthalmic pharmaceutical composition comprises:

(1) pilocarpine hydrochloride or pilocarpine nitrate at a concentration of 0.01% (w/w or w/v) to 0.4% (w/w or w/v), diclofenac sodium at a concentration of 0.001% (w/w or w/v) to 0.090% (w/w or w/v), and sodium hyaluronate at a concentration of 0.01% (w/w or w/v) to 0.9% (w/w or w/v);

(2) pilocarpine hydrochloride or pilocarpine nitrate at a concentration of 0.01% (w/w or w/v) to 0.4% (w/w or w/v), diclofenac sodium at a concentration of 0.001% (w/w or w/v) to 0.090% (w/w or w/v), and hydroxypropyl methylcellulose at a concentration of 0.1% (w/w or w/v) to 2.0% (w/w or w/v);

(3) pilocarpine hydrochloride or pilocarpine nitrate at a concentration of 0.01% (w/w or w/v) to 0.4% (w/w or w/v), ketorolac tromethamine at a concentration of 0.01% (w/w or w/v) to 0.60% (w/w or w/v), and sodium hyaluronate at a concentration of 0.01% (w/w or w/v) to 0.9% (w/w or w/v);

(4) pilocarpine hydrochloride or pilocarpine nitrate at a concentration of 0.01% (w/w or w/v) to 0.4% (w/w or w/v), ketorolac tromethamine at a concentration of 0.01% (w/w or w/v) to 0.60% (w/w or w/v), and hydroxypropyl methylcellulose at a concentration of 0.1% (w/w or w/v) to 2.0% (w/w or w/v); or (5) pilocarpine hydrochloride or pilocarpine nitrate at a concentration of 0.01% (w/w or w/v) to 0.4% (w/w or w/v), diclofenac sodium at a concentration of 0.001% (w/w or w/v) to 0.090% (w/w or w/v), sodium hyaluronate at a concentration of 0.01% (w/w or w/v) to 0.9% (w/w or w/v), and hydroxypropyl methylcellulose at a concentration of 0.1% (w/w or w/v) to 2.0% (w/w or w/v).

Embodiment 33. The method of embodiment 24, wherein the ophthalmic pharmaceutical composition is selected from compositions 1-32, and wherein each of compositions 1-32 comprises pilocarpine hydrochloride or pilocarpine nitrate, diclofenac sodium, and sodium hyaluronate as follows:

| Composition | pilocarpine hydrochloride or pilocarpine nitrate (w/w or w/v) | diclofenac sodium (w/w or w/v) | sodium hyaluronate (w/w or w/v) |
|---|---|---|---|
| 1 | 0.1% | 0% | 0% |
| 2 | 0.1% | 0.001% | 0% |
| 3 | 0.1% | 0.006% | 0% |
| 4 | 0.1% | 0.090% | 0% |
| 5 | 0.1% | 0% | 0.01% |
| 6 | 0.1% | 0% | 0.1% |
| 7 | 0.1% | 0% | 0.9% |
| 8 | 0.1% | 0.001% | 0.01% |
| 9 | 0.1% | 0.001% | 0.1% |
| 10 | 0.1% | 0.001% | 0.9% |
| 11 | 0.1% | 0.006% | 0.01% |
| 12 | 0.1% | 0.006% | 0.1% |
| 13 | 0.1% | 0.006% | 0.9% |
| 14 | 0.1% | 0.090% | 0.01% |
| 15 | 0.1% | 0.090% | 0.1% |
| 16 | 0.1% | 0.090% | 0.9% |
| 17 | 0.2% | 0% | 0% |
| 18 | 0.2% | 0.001% | 0% |
| 19 | 0.2% | 0.006% | 0% |
| 20 | 0.2% | 0.090% | 0% |
| 21 | 0.2% | 0% | 0.01% |
| 22 | 0.2% | 0% | 0.1% |
| 23 | 0.2% | 0% | 0.9% |
| 24 | 0.2% | 0.001% | 0.01% |
| 25 | 0.2% | 0.001% | 0.1% |
| 26 | 0.2% | 0.001% | 0.9% |
| 27 | 0.2% | 0.006% | 0.01% |
| 28 | 0.2% | 0.006% | 0.1% |
| 29 | 0.2% | 0.006% | 0.9% |
| 30 | 0.2% | 0.090% | 0.01% |
| 31 | 0.2% | 0.090% | 0.1% |
| 32 | 0.2% | 0.090% | 0.9% |

Embodiment 34. The method of embodiment 24, wherein the ophthalmic pharmaceutical composition is selected from compositions 33-64, and wherein each of compositions 33-64 comprises pilocarpine hydrochloride or pilocarpine nitrate, diclofenac sodium, and hydroxypropyl methylcellulose as follows:

| Composition | pilocarpine hydrochloride or pilocarpine nitrate (w/w or w/v) | diclofenac sodium (w/w or w/v) | hydroxypropyl methylcellulose (w/w or w/v) |
|---|---|---|---|
| 33 | 0.1% | 0% | 0% |
| 34 | 0.1% | 0.001% | 0% |
| 35 | 0.1% | 0.006% | 0% |
| 36 | 0.1% | 0.090% | 0% |
| 37 | 0.1% | 0% | 0.1% |
| 38 | 0.1% | 0% | 0.8% |
| 39 | 0.1% | 0% | 1.2% |
| 40 | 0.1% | 0.001% | 0.1% |
| 41 | 0.1% | 0.001% | 0.8% |
| 42 | 0.1% | 0.001% | 1.2% |
| 43 | 0.1% | 0.006% | 0.1% |
| 44 | 0.1% | 0.006% | 0.8% |
| 45 | 0.1% | 0.006% | 1.2% |
| 46 | 0.1% | 0.090% | 0.1% |
| 47 | 0.1% | 0.090% | 0.8% |
| 48 | 0.1% | 0.090% | 1.2% |
| 49 | 0.2% | 0% | 0% |
| 50 | 0.2% | 0.001% | 0% |
| 51 | 0.2% | 0.006% | 0% |
| 52 | 0.2% | 0.090% | 0% |
| 53 | 0.2% | 0% | 0.1% |
| 54 | 0.2% | 0% | 0.8% |
| 55 | 0.2% | 0% | 1.2% |
| 56 | 0.2% | 0.001% | 0.1% |
| 57 | 0.2% | 0.001% | 0.8% |
| 58 | 0.2% | 0.001% | 1.2% |
| 59 | 0.2% | 0.006% | 0.1% |
| 60 | 0.2% | 0.006% | 0.8% |
| 61 | 0.2% | 0.006% | 1.2% |
| 62 | 0.2% | 0.090% | 0.1% |
| 63 | 0.2% | 0.090% | 0.8% |
| 64 | 0.2% | 0.090% | 1.2% |

Embodiment 35. The method of embodiment 24, wherein the ophthalmic pharmaceutical composition is selected from compositions 65-96, and wherein each of compositions 65-96 comprises pilocarpine hydrochloride or pilocarpine nitrate, ketorolac tromethamine, and sodium hyaluronate as follows:

| Composition | pilocarpine hydrochloride or pilocarpine nitrate (w/w or w/v) | ketorolac tromethamine (w/w or w/v) | sodium hyaluronate (w/w or w/v) |
|---|---|---|---|
| 65 | 0.1% | 0% | 0% |
| 66 | 0.1% | 0.01% | 0% |
| 67 | 0.1% | 0.30% | 0% |
| 68 | 0.1% | 0.50% | 0% |
| 69 | 0.1% | 0% | 0.01% |
| 70 | 0.1% | 0% | 0.1% |
| 71 | 0.1% | 0% | 0.9% |
| 72 | 0.1% | 0.01% | 0.01% |
| 73 | 0.1% | 0.01% | 0.1% |
| 74 | 0.1% | 0.01% | 0.9% |
| 75 | 0.1% | 0.30% | 0.01% |
| 76 | 0.1% | 0.30% | 0.1% |
| 77 | 0.1% | 0.30% | 0.9% |
| 78 | 0.1% | 0.50% | 0.01% |
| 79 | 0.1% | 0.50% | 0.1% |
| 80 | 0.1% | 0.50% | 0.9% |
| 81 | 0.2% | 0% | 0% |
| 82 | 0.2% | 0.01% | 0% |
| 83 | 0.2% | 0.30% | 0% |
| 84 | 0.2% | 0.50% | 0% |
| 85 | 0.2% | 0% | 0.01% |

-continued

| Composition | pilocarpine hydrochloride or pilocarpine nitrate (w/w or w/v) | ketorolac tromethamine (w/w or w/v) | sodium hyaluronate (w/w or w/v) |
|---|---|---|---|
| 86 | 0.2% | 0% | 0.1% |
| 87 | 0.2% | 0% | 0.9% |
| 88 | 0.2% | 0.01% | 0.01% |
| 89 | 0.2% | 0.01% | 0.1% |
| 90 | 0.2% | 0.01% | 0.9% |
| 91 | 0.2% | 0.30% | 0.01% |
| 92 | 0.2% | 0.30% | 0.1% |
| 93 | 0.2% | 0.30% | 0.9% |
| 94 | 0.2% | 0.50% | 0.01% |
| 95 | 0.2% | 0.50% | 0.1% |
| 96 | 0.2% | 0.50% | 0.9% |

Embodiment 36. The method of embodiment 24, wherein the ophthalmic pharmaceutical composition is selected from compositions 97-128, and wherein each of compositions 97-128 comprises pilocarpine hydrochloride or pilocarpine nitrate, ketorolac tromethamine, and hydroxypropyl methylcellulose as follows:

| Composition | pilocarpine hydrochloride or pilocarpine nitrate (w/w or w/v) | ketorolac tromethamine (w/w or w/v) | hydroxypropyl methylcellulose (w/w or w/v) |
|---|---|---|---|
| 97 | 0.1% | 0% | 0% |
| 98 | 0.1% | 0.01% | 0% |
| 99 | 0.1% | 0.30% | 0% |
| 100 | 0.1% | 0.50% | 0% |
| 101 | 0.1% | 0% | 0.1% |
| 102 | 0.1% | 0% | 0.8% |
| 103 | 0.1% | 0% | 1.2% |
| 104 | 0.1% | 0.01% | 0.1% |
| 105 | 0.1% | 0.01% | 0.8% |
| 106 | 0.1% | 0.01% | 1.2% |
| 107 | 0.1% | 0.30% | 0.1% |
| 108 | 0.1% | 0.30% | 0.8% |
| 109 | 0.1% | 0.30% | 1.2% |
| 110 | 0.1% | 0.50% | 0.1% |
| 111 | 0.1% | 0.50% | 0.8% |
| 112 | 0.1% | 0.50% | 1.2% |
| 113 | 0.2% | 0% | 0% |
| 114 | 0.2% | 0.01% | 0% |
| 115 | 0.2% | 0.30% | 0% |
| 116 | 0.2% | 0.50% | 0% |
| 117 | 0.2% | 0% | 0.1% |
| 118 | 0.2% | 0% | 0.8% |
| 119 | 0.2% | 0% | 1.2% |
| 120 | 0.2% | 0.01% | 0.1% |
| 121 | 0.2% | 0.01% | 0.8% |
| 122 | 0.2% | 0.01% | 1.2% |
| 123 | 0.2% | 0.30% | 0.1% |
| 124 | 0.2% | 0.30% | 0.8% |
| 125 | 0.2% | 0.30% | 1.2% |
| 126 | 0.2% | 0.50% | 0.1% |
| 127 | 0.2% | 0.50% | 0.8% |
| 128 | 0.2% | 0.50% | 1.2% |

Embodiment 37. The method of embodiment 24, wherein the ophthalmic pharmaceutical composition is a slow release composition.

Embodiment 38. The method of embodiment 24, wherein the ophthalmic pharmaceutical composition is in the form of a suspension, gel, ointment, injectable solution, spray, or eye drop formulation.

Embodiment 39. The method of embodiment 24, wherein the ophthalmic pharmaceutical composition is suitable for implantation in or on a subject's eye or tissue surrounding the eye.

Embodiment 40. The method of embodiment 39, wherein the ophthalmic pharmaceutical composition is suitable for implantation into subconjunctival space, naso-lacrimal duct, or vitreous body of the subject.

Embodiment 41. The method of embodiment 24, wherein the ophthalmic pharmaceutical composition is suitable for topical delivery to a subject's eye or tissue surrounding the eye.

Embodiment 42. The method of embodiment 24, wherein the ophthalmic pharmaceutical composition comprises a pharmaceutically acceptable diluent, preservative, and/or solvent.

Embodiment 43. The method of embodiment 24, further comprising an isotonic agent, a wetting agent, a buffer, a stabilizer, a pH agent, a solubilizer, a thickening agent, and/or a dispersing agent.

Embodiment 44. The method of embodiment 24, wherein the ophthalmic pharmaceutical composition is effective for correction of presbyopia for up to 24 hours.

Embodiment 45. The method of embodiment 24, wherein the ophthalmic pharmaceutical composition corrects presbyopia without adversely affecting night vision.

Embodiment 46. The method of embodiment 24, wherein the ophthalmic pharmaceutical composition corrects presbyopia without adversely reducing visual field.

Embodiment 47. The method of embodiment 24, wherein the subject:

a) is a spectacle wearer who cannot or will not use progressive or bifocal lenses;

b) underwent cataract surgery; c) developed presbyopia after a corneal procedure; d) has mono-focal or multifocal intraocular lenses; e) uses contact lenses and does not tolerate mono-vision contact lenses;

f) uses contact lenses and does not tolerate multifocal contact lenses;

g) suffers from a higher order aberration after corneal surgery;

h) suffers from hyperopia or tropias;

i) does not tolerate a change in spectacle prescription;

j) experiences a rapid change in spectacle prescription;

k) is at risk of falls when using progressive or bifocal lenses; and/or l) suffers from a higher order aberration at night or under dull light conditions.

Embodiment 48. The method of embodiment 24, wherein the administration is topical or by surgical intervention.

Embodiment 49. The method of embodiment 48, wherein the surgical intervention comprises a step of administering the ophthalmic pharmaceutical composition in or on the subject's eye or tissue surrounding the eye.

Embodiment 50. The method of embodiment 49, wherein the ophthalmic pharmaceutical composition is administered into subconjunctival space, naso-lacrimal duct, or vitreous body of the subject.

Embodiment 51. A method of reducing the size of a pupil in a subject comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 52. A method of inducing miosis in a subject comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 53. A method of increasing the depth of field in a subject's eye comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 54. A method of decreasing the magnitude of higher order aberrations in a subject's eye comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 55. A method of improving uncorrected near and distance visual acuity in a subject comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 56. An implant comprising an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 57. A kit comprising an ophthalmic pharmaceutical composition comprising pilocarpine or a pharmaceutically acceptable salt thereof at a concentration of 0.01% (w/w or w/v) to 0.4% (w/w or w/v) and a pharmaceutically acceptable carrier.

Embodiment 58. A method of correcting presbyopia in a subject comprising administering to the subject a therapeutically effective amount of an ophthalmic pharmaceutical composition that reduces the size of pupil in the subject, wherein the ophthalmic pharmaceutical composition comprises pilocarpine or a pharmaceutically acceptable salt thereof at a concentration of 0.01% (w/w or w/v) to 0.4% (w/w or w/v) and a pharmaceutically acceptable carrier.

Embodiment 59. The method according to any one of embodiments 24-55, 58, 68, and 70, wherein the ophthalmic pharmaceutical composition is administered up to twice per application, up to three applications per day.

Embodiment 60. The ophthalmic pharmaceutical composition according to any one of embodiments 1-23, 67 and 69 for use in a method of correcting presbyopia in a subject, comprising administering the ophthalmic pharmaceutical composition to the subject's eye topically or by surgical intervention.

Embodiment 61. The ophthalmic pharmaceutical composition according to any one of embodiments 1-23, 67 and 69 for use in a method of reducing the size of a pupil in a subject, comprising administering the ophthalmic pharmaceutical composition to the subject's eye topically or by surgical intervention.

Embodiment 62. The ophthalmic pharmaceutical composition according to any one of embodiments 1-23, 67 and 69 for use in a method of inducing miosis in a subject, comprising administering the ophthalmic pharmaceutical composition to the subject's eye topically or by surgical intervention.

Embodiment 63. The ophthalmic pharmaceutical composition according to any one of embodiments 1-23, 67 and 69 for use in a method of increasing the depth of field in a subject's eye, comprising administering the ophthalmic pharmaceutical composition to the subject's eye topically or by surgical intervention.

Embodiment 64. The ophthalmic pharmaceutical composition according to any one of embodiments 1-23, 67 and 69 for use in a method of decreasing the magnitude of higher order aberrations in a subject's eye, comprising administering the ophthalmic pharmaceutical composition to the subject's eye topically or by surgical intervention.

Embodiment 65. The ophthalmic pharmaceutical composition according to any one of embodiments 1-23, 67 and 69 for use in a method of improving uncorrected near and distance visual acuity in a subject, comprising administering the ophthalmic pharmaceutical composition to the subject's eye topically or by surgical intervention.

Embodiment 66. The ophthalmic pharmaceutical composition according to any one of embodiments 1-23, 67 and 69 for use in a method of treating a human or animal body.

Embodiment 67. The ophthalmic pharmaceutical composition of embodiment 1, wherein the ophthalmic pharmaceutical composition corrects presbyopia without adversely reducing distance visual acuity.

Embodiment 68. The method of embodiment 24, wherein the ophthalmic pharmaceutical composition corrects presbyopia without adversely reducing distance visual acuity.

Embodiment 69. The ophthalmic pharmaceutical composition of embodiment 10, wherein the ophthalmic pharmaceutical composition is selected from any one of compositions 1-32, further comprising hydroxypropyl methylcellulose at a concentration of 0.1% (w/w or w/v), 0.8% (w/w or w/v), or 1.2% (w/w or w/v).

Embodiment 70. The method of embodiment 33, wherein the ophthalmic pharmaceutical composition is selected from any one of compositions 1-32, further comprising hydroxypropyl methylcellulose at a concentration of 0.1% (w/w or w/v), 0.8% (w/w or w/v), or 1.2% (w/w or w/v).

Embodiment 71. An ophthalmic pharmaceutical composition comprising pilocarpine or a pharmaceutically acceptable salt thereof at a concentration of 0.01% (w/w or w/v) to 0.4% (w/w or w/v), hydroxypropyl methylcellulose at a concentration of 0.1% (w/w or w/v) to 2.0% (w/w or w/v), and a pharmaceutically acceptable carrier.

Embodiment 72. The ophthalmic pharmaceutical composition of embodiment 71, wherein the pilocarpine salt is pilocarpine hydrochloride or pilocarpine nitrate.

Embodiment 73. The ophthalmic pharmaceutical composition of embodiment 72, further comprising sodium hyaluronate at a concentration of 0.01% (w/w or w/v) to 0.9% (w/w or w/v).

Embodiment 74. The ophthalmic pharmaceutical composition of embodiment 73, further comprising diclofenac or a pharmaceutically acceptable salt thereof at a concentration of 0.001% (w/w or w/v) to 0.090% (w/w or w/v), or ketorolac or a pharmaceutically acceptable salt thereof at a concentration of 0.01% (w/w or w/v) to 0.60% (w/w or w/v).

Embodiment 75. The ophthalmic pharmaceutical composition of embodiment 74, wherein the diclofenac salt is diclofenac sodium, or wherein the ketorolac salt is ketorolac tromethamine.

Embodiment 76. The ophthalmic pharmaceutical composition of embodiment 75, wherein the ophthalmic pharmaceutical composition comprises:

(1) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), sodium hyaluronate at a concentration of 0.01% (w/w or w/v) to 0.2% (w/w or w/v), and diclofenac sodium at a concentration of 0.001% (w/w or w/v) to 0.012% (w/w or w/v); or (2) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), sodium hyaluronate at a concentration of 0.01% (w/w or w/v) to 0.2% (w/w or w/v), and ketorolac tromethamine at a concentration of 0.01% (w/w or w/v) to 0.50% (w/w or w/v).

Embodiment 77. The ophthalmic pharmaceutical composition of embodiment 76, wherein the ophthalmic pharmaceutical composition comprises:

(1) pilocarpine hydrochloride or pilocarpine nitrate at a concentration of 0.2% (w/w or w/v), hydroxypropyl methylcellulose at a concentration of 0.8% (w/w or w/v), sodium hyaluronate at a concentration of 0.1% (w/w or w/v), and diclofenac sodium at a concentration of 0.006% (w/w or w/v); or (2) pilocarpine hydrochloride or pilocarpine nitrate at a concentration of 0.2% (w/w or w/v), hydroxypropyl methylcellulose at a concentration of 0.8% (w/w or w/v), sodium hyaluronate at a concentration of 0.1% (w/w or w/v), and ketorolac tromethamine at a concentration of 0.50% (w/w or w/v).

Embodiment 78. The ophthalmic pharmaceutical composition of embodiment 72, further comprising:

(1) sodium hyaluronate at a concentration of 0.01% (w/w or w/v) to 0.9% (w/w or w/v), or diclofenac sodium at a concentration of 0.001% (w/w or w/v) to 0.090% (w/w or w/v), or mixtures thereof; or (2) sodium hyaluronate at a concentration of 0.01% (w/w or w/v) to 0.9% (w/w or w/v), or ketorolac tromethamine at a concentration of 0.01% (w/w or w/v) to 0.60% (w/w or w/v), or mixtures thereof.

Embodiment 79. The ophthalmic pharmaceutical composition of embodiment 72, wherein the ophthalmic pharmaceutical composition comprises:

(1) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), and further comprising sodium hyaluronate at a concentration of 0.01% (w/w or w/v) to 0.2% (w/w or w/v), or diclofenac sodium at a concentration of 0.001% (w/w or w/v) to 0.012% (w/w or w/v), or mixtures thereof; or (2) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), and further comprising sodium hyaluronate at a concentration of 0.01% (w/w or w/v) to 0.2% (w/w or w/v), or ketorolac tromethamine at a concentration of 0.01% (w/w or w/v) to 0.50% (w/w or w/v), or mixtures thereof.

Embodiment 80. The ophthalmic pharmaceutical composition of embodiment 79, wherein the ophthalmic pharmaceutical composition comprises:

(1) pilocarpine hydrochloride or pilocarpine nitrate at a concentration of 0.2% (w/w or w/v), hydroxypropyl methylcellulose at a concentration of 0.8% (w/w or w/v), and further comprising sodium hyaluronate at a concentration of 0.1% (w/w or w/v), or diclofenac sodium at a concentration of 0.006% (w/w or w/v), or mixtures thereof; or (2) pilocarpine hydrochloride or pilocarpine nitrate at a concentration of 0.2% (w/w or w/v), hydroxypropyl methylcellulose at a concentration of 0.8% (w/w or w/v), and further comprising sodium hyaluronate at a concentration of 0.1% (w/w or w/v), or ketorolac tromethamine at a concentration of 0.50% (w/w or w/v), or mixtures thereof.

Embodiment 81. The ophthalmic pharmaceutical composition of embodiment 71, wherein the ophthalmic pharmaceutical composition comprises a pharmaceutically acceptable diluent, preservative, and/or solvent.

Embodiment 82. The ophthalmic pharmaceutical composition of embodiment 71, further comprising an isotonic agent, a wetting agent, a buffer, a stabilizer, a pH agent, a solubilizer, a thickening agent, and/or a dispersing agent.

Embodiment 83. The ophthalmic pharmaceutical composition of embodiment 71, wherein the ophthalmic pharmaceutical composition is effective for correction of presbyopia for up to 24 hours.

Embodiment 84. A method of correcting presbyopia in a subject comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v), hydroxypropyl methylcellulose at a concentration of 0.1% (w/w or w/v) to 2.0% (w/w or w/v), and a pharmaceutically acceptable carrier.

Embodiment 85. The method of embodiment 84, wherein the pilocarpine salt is pilocarpine hydrochloride or pilocarpine nitrate.

Embodiment 86. The method of embodiment 85, wherein the ophthalmic pharmaceutical composition further comprises sodium hyaluronate at a concentration of 0.01% (w/w or w/v) to 0.9% (w/w or w/v).

Embodiment 87. The method of embodiment 86, wherein the ophthalmic pharmaceutical composition further comprises diclofenac or a pharmaceutically acceptable salt thereof at a concentration of 0.001% (w/w or w/v) to 0.090% (w/w or w/v), or ketorolac or a pharmaceutically acceptable salt thereof at a concentration of 0.01% (w/w or w/v) to 0.60% (w/w or w/v).

Embodiment 88. The method of embodiment 87, wherein the diclofenac salt is diclofenac sodium, or wherein the ketorolac salt is ketorolac tromethamine.

Embodiment 89. The method of embodiment 88, wherein the ophthalmic pharmaceutical composition comprises:

(1) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), sodium hyaluronate at a concentration of 0.01% (w/w or w/v) to 0.2% (w/w or w/v), and diclofenac sodium at a concentration of 0.001% (w/w or w/v) to 0.012% (w/w or w/v); or (2) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), sodium hyaluronate at a concentration of 0.01% (w/w or w/v) to 0.2% (w/w or w/v), and ketorolac tromethamine at a concentration of 0.01% (w/w or w/v) to 0.50% (w/w or w/v).

Embodiment 90. The method of embodiment 89, wherein the ophthalmic pharmaceutical composition comprises:

(1) pilocarpine hydrochloride or pilocarpine nitrate at a concentration of 0.2% (w/w or w/v), hydroxypropyl methylcellulose at a concentration of 0.8% (w/w or w/v), sodium hyaluronate at a concentration of 0.1% (w/w or w/v), and diclofenac sodium at a concentration of 0.006% (w/w or w/v); or (2) pilocarpine hydrochloride or pilocarpine nitrate at a concentration of 0.2% (w/w or w/v), hydroxypropyl methylcellulose at a concentration of 0.8% (w/w or w/v), sodium hyaluronate at a concentration of 0.1% (w/w or w/v), and ketorolac tromethamine at a concentration of 0.50% (w/w or w/v).

Embodiment 91. The method of embodiment 85, wherein the ophthalmic pharmaceutical composition further comprises:

(1) sodium hyaluronate at a concentration of 0.01% (w/w or w/v) to 0.9% (w/w or w/v), or diclofenac sodium at a concentration of 0.001% (w/w or w/v) to 0.090% (w/w or w/v), or mixtures thereof; or (2) sodium hyaluronate at a concentration of 0.01% (w/w or w/v) to 0.9% (w/w or w/v), or ketorolac tromethamine at a concentration of 0.01% (w/w or w/v) to 0.60% (w/w or w/v), or mixtures thereof.

Embodiment 92. The method of embodiment 85, wherein the ophthalmic pharmaceutical composition comprises:

(1) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), and further comprising sodium hyaluronate at a concentration of 0.01% (w/w or w/v) to 0.2% (w/w or w/v), or diclofenac sodium at a concentration of 0.001% (w/w or w/v) to 0.012% (w/w or w/v), or mixtures thereof; or (2) pilocarpine hydrochloride or pilocarpine nitrate at a concentration of 0.1% (w/w or w/v) to 0.4% (w/w or w/v), hydroxypropyl methylcellulose at a concentration of 0.1% (w/w or w/v) to 1.2% (w/w or w/v), and further comprising sodium hyaluronate at a concentration of 0.01% (w/w or w/v) to 0.2% (w/w or w/v), or ketorolac tromethamine at a concentration of 0.01% (w/w or w/v) to 0.50% (w/w or w/v), or mixtures thereof.

Embodiment 93. The method of embodiment 92, wherein the ophthalmic pharmaceutical composition comprises:

(1) pilocarpine hydrochloride or pilocarpine nitrate at a concentration of 0.2% (w/w or w/v), hydroxypropyl methylcellulose at a concentration of 0.8% (w/w or w/v), and further comprising sodium hyaluronate at a concentration of 0.1% (w/w or w/v), or diclofenac sodium at a concentration of 0.006% (w/w or w/v), or mixtures thereof; or (2) pilocarpine hydrochloride or pilocarpine nitrate at a concentration of 0.2% (w/w or w/v), hydroxypropyl methylcellulose at a concentration of 0.8% (w/w or w/v), and further comprising sodium hyaluronate at a concentration of 0.1% (w/w or w/v), or ketorolac tromethamine at a concentration of 0.50% (w/w or w/v), or mixtures thereof.

Embodiment 94. The method of embodiment 85, wherein the ophthalmic pharmaceutical composition comprises a pharmaceutically acceptable diluent, preservative, and/or solvent.

Embodiment 95. The method of embodiment 85, wherein the ophthalmic pharmaceutical composition further comprises an isotonic agent, a wetting agent, a buffer, a stabilizer, a pH agent, a solubilizer, a thickening agent, and/or a dispersing agent.

Embodiment 96. The method of embodiment 85, wherein the ophthalmic pharmaceutical composition is effective for correction of presbyopia for up to 24 hours.

Embodiment 97. The method of embodiment 85, wherein the administration is topical or by surgical intervention.

Embodiment 98. The method of embodiment 85, wherein the subject:

a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

Embodiment 99. A method of reducing the size of a pupil in a subject comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v), hydroxypropyl methylcellulose at a concentration of 0.1% (w/w or w/v) to 2.0% (w/w or w/v), and a pharmaceutically acceptable carrier.

Embodiment 100. A method of increasing the depth of field in a subject's eye comprising administering to the subject a therapeutically effective amount of an ophthalmic pharmaceutical composition comprising pilocarpine or a pharmaceutically acceptable salt thereof at a concentration of 0.01% (w/w or w/v) to 0.4% (w/w or w/v), hydroxypropyl methylcellulose at a concentration of 0.1% (w/w or w/v) to 2.0% (w/w or w/v), and a pharmaceutically acceptable carrier.

DESCRIPTION OF DRAWINGS

Those of skilled in the art will understand that the drawings, described below, are for illustrative purposes only. The drawings are not intended to limit the scope of the present teachings in any way.

DETAILED DESCRIPTION

Figure 1:
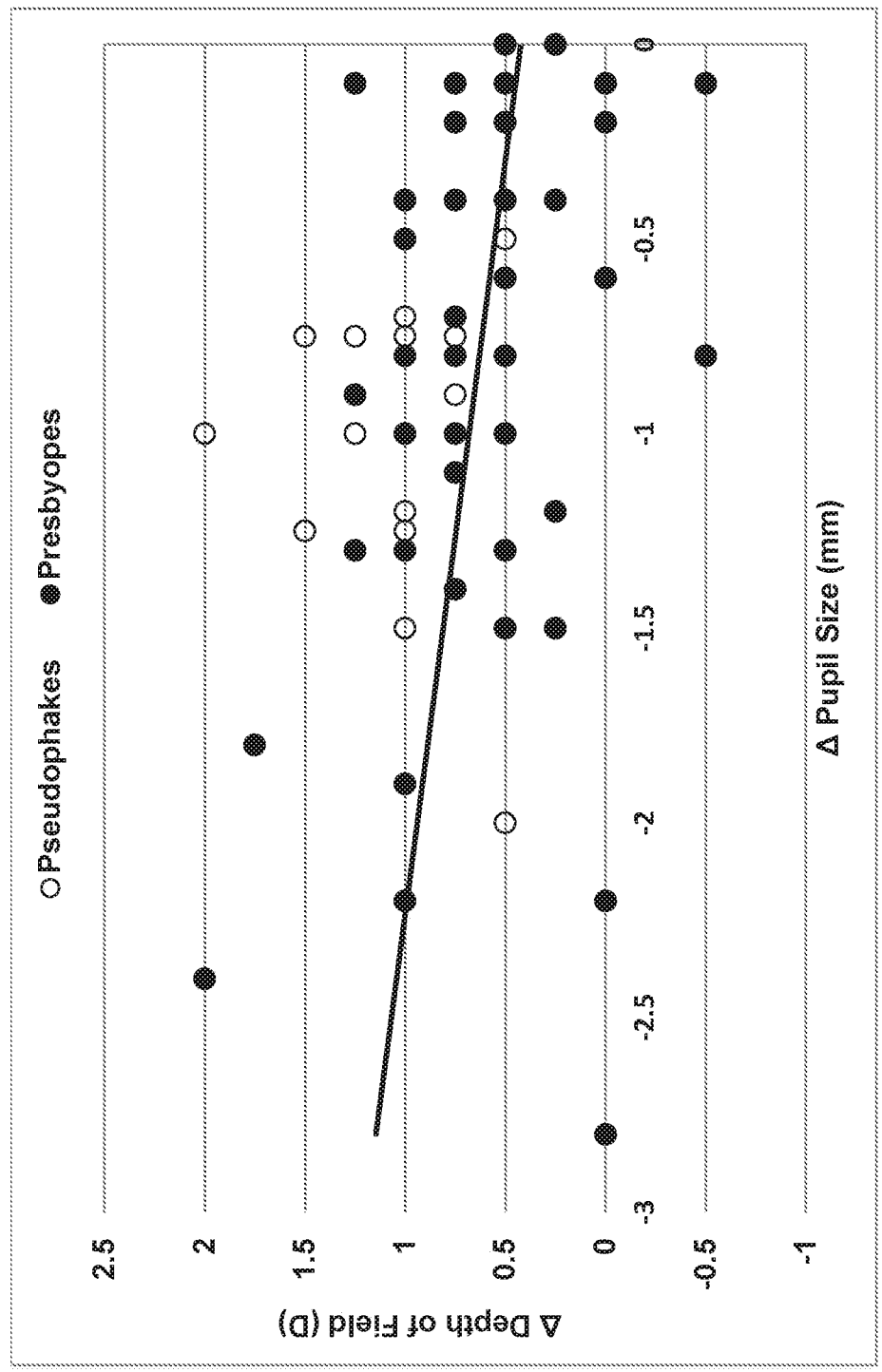
FIG. 1 illustrates the relationship between change in depth of field ($\Delta$DoF) and change in pupil size ($\Delta$pupil) in presbyopic group (filled circle) and the pseudophakic group (open circle) looking at a distant letters (6m) after drop instillation of an ophthalmic pharmaceutical composition according to this disclosure.

Many modifications and other embodiments of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Definitions

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of ophthalmic pharmaceutical preparations and uses, which are within the skill of the art. The materials, methods and examples are illustrative only and not limiting. The following is presented by way of illustration and is not intended to limit the scope of the disclosure.

For convenience, certain terms employed in the entire application (including the specification, examples, and appended claims) are collected here.

As used herein, the singular forms "a" "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in the same manner as the term "comprising."

As used herein, the term "administering" refers to the placement of an ophthalmic pharmaceutical composition into a subject by a method or route that results in at least partial localization of the pharmaceutical composition at a desired site or tissue location (e.g., on a subject's eye or tissue surrounding the eye). For example, a composition may be administered topically to a subject's eye or tissue surrounding the eye. Alternatively, a composition may be administered through surgical intervention in or on a subject's eye or tissue surrounding the eye. In some embodiments of this disclosure, the ophthalmic pharmaceutical composition may be administered by any appropriate route that results in effective treatment in the subject, i.e. administration results in delivery to a desired location or tissue in the subject where at least a portion of the pilocarpine or a pharmaceutically acceptable salt is located at a desired site or tissue location. In some embodiments of this disclosure, the ophthalmic pharmaceutical composition may be administered several times in a short time period, e.g., within few seconds or minutes. For example, in some embodiments, the ophthalmic pharmaceutical composition may be administered twice within 2 seconds, 5 seconds, 10 seconds, 30 seconds, 1 minute, 5 minutes, 10 minutes, 20 minutes, or 30 minutes. In some embodiments, the ophthalmic pharmaceutical composition may be administered 3 times within 2 second, 5 seconds, 10 seconds, 30 seconds, 1 minute, 5 minutes, 10 minutes, 20 minutes, or 30 minutes. In some embodiments, the ophthalmic pharmaceutical composition may be administered 4 times within 2 seconds, 5 seconds, 10 seconds, 30 seconds, 1 minute, 5 minutes, 10 minutes, 20 minutes, or 30 minutes.

The term "composition" refers to a mixture that contains a therapeutically active component(s) and a carrier or excipient, such as a pharmaceutically acceptable carrier or excipient that is conventional in the art and which is suitable for administration to a subject for intended therapeutic purposes. The therapeutically active component may include for example, pilocarpine or a pharmaceutically acceptable salt of the disclosure. In some embodiments, the composition may be in the form of a suspension, gel, ointment, injectable solution, spray, or eye drop formulation (i.e., compositions that are suitable for administration as eye drops). In some embodiments, when the composition is in the form of an eye drop formulation, each eye drop solution may be in the volume of from about 5 microliters to about 10 microliters, from about 10 microliters to about 20 microliters, from about 20 microliters to about 50 microliters, from about 50 microliters to about 100 microliters, from about 100 microliters to about 250 microliters, or from about 250 microliters to about 500 microliters.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition that "comprises," "has" or "includes" one or more features is not limited to possessing only those one or more features and can cover other unlisted features. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element as essential to the practice of the present disclosure.

The term "consisting essentially of" allows for the presence of additional materials or steps that "do not materially affect the basic and novel characteristic(s)" of the claimed invention.

The term "consisting of" refers to compositions, methods, and respective components thereof as described herein, which are exclusive of any element not recited in that description of the embodiment.

As used herein, the terms "correct," "correcting," or "correction" refers to a decrease or amelioration in the severity of presbyopia. The amelioration may be complete, e.g., the total absence of presbyopia. The amelioration may also be partial, such that the amount of presbyopia is less than that which would have been present without the exposure to the methods and compositions of the present disclosure. The extent of presbyopia may be determined by any method known in the art for ophthalmic examination.

The phrase "ophthalmically acceptable" is employed herein to refer to those compounds, materials, compositions, and/or dosage forms which are, within the scope of sound medical judgment, suitable for use in contact with the eye and surrounding tissues of human beings and animals without excessive toxicity, irritation, allergic response, or other problem or complication, commensurate with a reasonable benefit/risk ratio. Drug-approval agencies (e.g., EMA, US-FDA) provide guidance and approve pharmaceutically acceptable compounds, materials, compositions, and/or dosage forms. Examples may be found in Pharmacopeias.

The phrase "ophthalmically acceptable carrier" is employed herein to refer to a pharmaceutically acceptable material chosen from a solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof, that are compatible with pharmaceutical administration. The use of such media and agents for pharmaceutically active substances is well known in the ophthalmical art. The compositions may also contain other active compounds providing supplemental, additional, or enhanced therapeutic functions.

The phrase "ophthalmic pharmaceutical composition" refers to a pharmaceutical composition that is useful for manufacturing a medicament to be administered to an eye of a mammal.

The term "pharmaceutically acceptable salt(s)" refers to salts of acidic or basic groups that may be present in compounds used in the present compositions. Pharmaceutically acceptable salts are well known in the art. Examples of pharmaceutically acceptable, nontoxic acid addition salts are salts of an amino group formed with inorganic acids such as hydrochloric acid, hydrobromic acid, phosphoric acid, sulfuric acid and perchloric add or with organic acids such as acetic acid, oxalic acid, maleic acid, tartaric acid, citric acid, succinic acid or malonic acid. Other pharmaceutically acceptable salts include sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate salts, and the like. For example, in some embodiments, the ophthalmic pharmaceutical composition comprises pilocarpine hydrochloride or pilocarpine nitrate. On the other hand, certain compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. For example, in some embodiments, the ophthalmic pharmaceutical composition comprises diclofenac sodium. For example, in some embodiments, the ophthalmic pharmaceutical composition comprises ketorolac tromethamine.

The term "statistically significant" or "significantly" refers to statistical significance. The term refers to statistical evidence that there is a difference. It can be defined as the probability of making a decision to reject the null hypothesis when the null hypothesis is actually true. The decision is often made using the p-value. Any other measure of significant significance that is well known in the art can be used.

The terms "subject" and "individual" are used interchangeably herein, and refer to an animal, for example a human, to whom treatment, with methods and compositions described herein, is or are provided. In some embodiments, the subject is a human.

The term "therapeutically effective amount" as used herein refers to the amount of therapeutic agent (for example, pilocarpine or a pharmaceutically acceptable salt) or pharmaceutical composition, sufficient to reduce at least one or more symptom(s) of the disease or disorder, or to provide the desired effect. For example, it can be the amount that temporarily ameliorate, or even eliminate presbyopia such that the near vision of the treated eye is temporarily restored partially or completely. For example, it may be the amount that causes a significant reduction in discomfort or risk of falls when using progressive or bifocal lenses. For example, it may be the amount that diminishes or complete relieves blurring and dimness after eye surgery.

As used herein, the terms "treat," "treatment," or "treating" refers to an amelioration or elimination of a disease or disorder, or at least one discernible symptom thereof. In some embodiments, "treatment" or "treating" refers to an amelioration or elimination of at least one measurable physical parameter, not necessarily discernible by the patient. For example, the treatment may enable the patient to visually focus on objects at a nearby distance, including objects at a distance around a normal reading distance. In some embodiments, the treatment is effective to ameliorate or eliminate presbyopia for about 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, or 1 hour. In some embodiments, the treatment is effective to ameliorate or eliminate presbyopia for up to 24 hours. The extent of presbyopia can be determined by any method known in the art for ophthalmic examination.

For example, in one embodiment, treatment is measured by a subject's uncorrected distance and near visual acuity, which may be taken using a standard acceptable eye chart, for example Snellen chart at distance and Jaeger charts at near, or an early treatment diabetic retinopathy study (ETDRS) chart. All values can be converted to decimal notation using Halliday's conversion chart.

In another embodiment, treatment is measured by clinical evaluation of the depth of field, which may be obtained either using standard wavefront aberrometry or according to the following instructions:

Distance: best distance spectacle prescription in refractor head/trial frame. Look at 6/9 (0.6) Snellen letter. Increase plus sphere power until subject reports blur (+a Dioptres). Repeat using negative lenses (−b Dioptres). Remove negative sign in front of b. Depth of field at distance=(a+b) Dioptres.

Near: best distance spectacle prescription +2.5 Dioptres addition in refractor head/trial frame. Look at J2 print at 40 cm. Increase plus sphere power until subject reports blur (+x Dioptres). Repeat using negative lenses (−y Dioptres). Remove negative sign in front of y. Depth of field at near=(x+y) Dioptres.

In yet another embodiment, treatment is measured by change of pupil size, which may be evaluated by the infrared imaging system used for checking alignment during autorefractometry. The infrared image of the pupil converted to visible light, magnified and displayed on the instrument's viewing screen allows the user to observe the pupil and align the instrument during normal use. The vertical and horizontal pupil diameters can be measured on screen with a ruler as the subject glanced at the infinity target. The average of the two measurements can be recorded and corrected for magnification (approximately ×7 to ×8) for both vertical and horizontal meridia. The pupil size can also be measured by aberrometer and pupilometer.

In yet another embodiment, treatment is measured by pupil appearance, which can include inspecting the pupils for equal size (1 mm or less of difference may be normal), regular shape, reactivity to light, and direct and consensual accommodation.

In yet another embodiment, treatment is measured by non-invasive objective assessments of the $3^{rd}$, $4^{th}$ and $5^{th}$ ocular higher order aberrations (such as coma, spherical aberration, and trefoil), which may be conducted using standard wavefront aberrometry.

It should be understood that this disclosure is not limited to the particular methodology, protocols, and reagents, etc., described herein and as such can vary. The terminology used herein is for the purpose of describing particular embodiments only, and is not intended to limit the scope of the present disclosure, which is defined solely by the claims.

Pharmacological Treatment for Presbyopia

Presbyopia is typically age-related eye deterioration. Presbyopia normally develops decreased ability to focus on objects at close distances because of a gradual loss of accommodative amplitude. A presbyopic eye loses the ability to rapidly and easily focus on objects at near distances.

By way of background, when a young emmetrope fixates on a near object two main changes occur in the eye: accommodation and miosis. Accommodation is a change in crystalline lens refractive power. The lens becomes rounder, by which its refractive power increases. Miosis is a decrease in pupil size by which depth of field increases and high order aberrations decrease.

At a molecular level, both miosis and accommodation occur under the influence of the parasympathetic nervous system. The binding of parasympathomimetic drugs to muscarinic receptors induces muscular contraction of the ciliary muscle and the sphincter of the pupil, and increases the refractive power of the eye. If this stimulation is strong enough, some of the loss of the ability of the crystalline lens to change shape and position that normally occurs with age could be overcome while this stimulation is in place.

Presbyopia has been corrected with the use of spectacles, contact lenses or intra-ocular implants, and corneal ablation or inlays. The surgical methods that have been proposed to correct presbyopia do not completely restore the natural accommodative functionality of the eye that has been reduced either by natural ageing or by other means. Pharmacological treatments have been proposed to restore the natural loss of the accommodative functionality of the eye that leads to presbyopia.

To date, no clinically effective pharmaceutical preparations are available to treat the symptoms of presbyopia. The present disclosure provides for simple, convenient, and comfortable to use compositions and methods for patients suffering from the symptoms of presbyopia.

Ophthalmic Compositions of the Disclosure

According to the present disclosure, an ophthalmic pharmaceutical composition comprises a therapeutically effective amount of a parasympathomimetic drug or a pharmaceutically acceptable salt thereof.

The parasympathomimetic drug is intended to include any cholinergic drug that enhances the effects mediated by acetylcholine in the central nervous system, the peripheral nervous system, or both. One example of such parasympathomimetic drugs is pilocarpine. Additional examples are disclosed in U.S. Pat. No. 8,299,079 and may include acetylcholine, muscarine, nicotine, suxamethonium, bethanechol, methacholine, phenylpropanolamine, amphetamine, ephedrine, carbachol, phentolamine, and fenfluramine. In some embodiments, the parasympathomimetic drug is pilocarpine or carbachol. In preferred embodiments, the parasympathomimetic drug is pilocarpine.

Pilocarpine in the hydrochloride or nitrate form is a miotic that has been used in drop form for several decades to treat glaucoma. Long term topical application of certain concentrations of pilocarpine has been associated with several undesirable ocular and systemic adverse side effects, for example, pigment dispersion, dry eye, inflammation of the uveal tract, posterior synechia, ciliary muscle spasm, blurred vision, miosis, accommodative spasm, frontal headaches, twitching lids, conjunctival injection, cataract, iridic cysts, retinal detachment, nausea, vomiting, salivation, lacrimation, sweating, pulmonary edema, and bronchial spasm. (Havener, 1970, WH Ocular Pharmacology $2^{nd}$ ed. CV Mosby & Co, USA, pp. 207-243; Zimmer and Wheeler, 1982, Ophthalmology 89:76-80; Nuzzi et al., 1998, Int Ophthalmol 22:31-35; Pop et al., 2000, Oftalmologia 52:44-48; Diestelhorst, 2000, Graefes Arch Clin Exp Ophthalmol 238:433-439; Nordmann et al., 2000, Br J Ophthalmol 84:181-185). These adverse effects are generally associated with chronic use of 1% pilocarpine, or greater concentration, on a regular basis with several doses every day. Furthermore, the effect of pilocarpine on the pupil is affected by the colour and pigmentation of the iris (Barbee and Smith, 1957, Am J Ophthalmol 44:617-622; Harris and Galpin, 1971, Am J Ophthalmol 72:923-925; Smith et al., 1978, Brit J Ophthalmol 62:314-317).

In some embodiments, an ophthalmic pharmaceutical composition comprises a pharmaceutically acceptable salt of a parasympathomimetic drug. Accordingly, in some embodiments, an ophthalmic pharmaceutical composition comprises a pharmaceutically acceptable salt of pilocarpine or carbachol. In preferred embodiments, an ophthalmic pharmaceutical composition comprises pilocarpine hydrochloride or pilocarpine nitrate.

In some embodiments of ophthalmic pharmaceutical compositions, the pilocarpine or a pharmaceutically acceptable salt may be present in the amount of from about 0.01% to about 0.4%, from about 0.01% to about 0.35%, from about 0.01% to about 0.3%, from about 0.01% to about 0.25%, from about 0.01% to about 0.2%, from about 0.01% to about 0.15%, from about 0.01% to about 0.1%, from about 0.01% to about 0.05%, from about 0.05% to about 0.4%, from about 0.05% to about 0.35%, from about 0.05% to about 0.3%, from about 0.05% to about 0.25%, from about 0.05% to about 0.2%, from about 0.05% to about 0.15%, from about 0.05% to about 0.1%, from about 0.1% to about 0.4%, from about 0.1% to about 0.35%, from about 0.1% to about 0.3%, from about 0.1% to about 0.25%, from about 0.1% to about 0.2%, from about 0.1% to about 0.15%, from about 0.15% to about 0.4%, from about 0.15% to about 0.35%, from about 0.15% to about 0.3%, from about 0.15% to about 0.25%, from about 0.15% to about 0.2%, from about 0.2% to about 0.4%, from about 0.2% to about 0.35%, from about 0.2% to about 0.3%, from about 0.2% to about 0.25%, from about 0.25% to about 0.4%, from about 0.25% to about 0.35%, from about 0.25% to about 0.3%, from about 0.3% to about 0.4%, from about 0.3% to about 0.35%, from about 0.35% to about 0.4%, or at about 0.01%, about 0.05%, about 0.1%, about 0.15%, about 0.2%, about 0.25%, about 0.3%, about 0.35%, about 0.4%. In all of these embodiments, the percentile numbers are determined by weight (w/w). Alternatively, in all of these embodiments, the percentile numbers are determined by volume (w/v).

In some embodiments, an ophthalmic pharmaceutical composition may further comprise a non-steroid anti-inflammatory drug (NSAID) or a pharmaceutically acceptable salt thereof. The NSAID may reduce or eliminate local inflammation that could occur due to stimulation caused by a parasympathomimetic drug (e.g., pilocarpine).

The NSAIDs are well known in the art. In some embodiments, a suitable NSAID is diclofenac. Additional examples of NSAIDs include nepafenac, meloxicam, ketorolac, bromfenac, bendazac, flurbiprofen, suprofen, pranoprofen, oxyphenbutazone, surprofen, and indomethacin. Accordingly, in some embodiments, an ophthalmic pharmaceutical composition further comprises diclofenac. In some embodiments, an ophthalmic pharmaceutical composition further comprises ketorolac. Alternatively, an ophthalmic pharmaceutical composition may not comprise a NSAID.

In some embodiments, an ophthalmic pharmaceutical composition may further comprise a pharmaceutically acceptable salt of a NSAID. Non-limiting examples of such salts include alkali metal or alkaline earth metal salts and, particularly, calcium, magnesium, sodium, lithium, zinc, potassium, and iron salts. For example, in some embodiments, the ophthalmic pharmaceutical composition further comprises diclofenac sodium. In some embodiments, an ophthalmic pharmaceutical composition further comprises ketorolac tromethamine. Alternatively, an ophthalmic pharmaceutical composition may not comprise a pharmaceutically acceptable salt of a NSAID.

In some embodiments of ophthalmic pharmaceutical compositions, diclofenac or a pharmaceutically acceptable salt thereof (e.g., diclofenac sodium) may be present in the amount of from about 0.001% to about 0.090%, from about 0.001% to about 0.080%, from about 0.001% to about 0.070%, from about 0.001% to about 0.060%, from about 0.001% to about 0.050%, from about 0.001% to about 0.040%, from about 0.001% to about 0.030%, from about 0.001% to about 0.020%, about 0.001% to about 0.012%, from about 0.001% to about 0.011%, from about 0.001% to about 0.010%, from about 0.001% to about 0.009%, from about 0.001% to about 0.008%, from about 0.001% to about 0.007%, from about 0.001% to about 0.006%, from about 0.001% to about 0.005%, from about 0.001% to about 0.003%, from about 0.003% to about 0.090%, from about 0.003% to about 0.080%, from about 0.003% to about 0.070%, from about 0.003% to about 0.060%, from about 0.003% to about 0.050%, from about 0.003% to about 0.040%, from about 0.003% to about 0.030%, from about 0.003% to about 0.020%, about 0.003% to about 0.012%, from about 0.003% to about 0.011%, from about 0.003% to about 0.010%, from about 0.003% to about 0.009%, from about 0.003% to about 0.008%, from about 0.003% to about 0.007%, from about 0.003% to about 0.006%, from about 0.003% to about 0.005%, from about 0.005% to about 0.090%, from about 0.005% to about 0.080%, from about 0.005% to about 0.070%, from about 0.005% to about 0.060%, from about 0.005% to about 0.050%, from about 0.005% to about 0.040%, from about 0.005% to about 0.030%, from about 0.005% to about 0.020%, about 0.005% to about 0.012%, from about 0.005% to about 0.011%, from about 0.005% to about 0.010%, from about 0.005% to about 0.009%, from about 0.005% to about 0.008%, from about 0.005% to about 0.007%, from about 0.005% to about 0.006%, from about 0.006% to about 0.090%, from about 0.006% to about 0.080%, from about 0.006% to about 0.070%, from about 0.006% to about 0.060%, from about 0.006% to about 0.050%, from about 0.006% to about 0.040%, from about 0.006% to about 0.030%, from about 0.006% to about 0.020%, about 0.006% to about 0.012%, from about 0.006% to about 0.011%, from about 0.006% to about 0.010%, from about 0.006% to about 0.009%, from about 0.006% to about 0.008%, from about 0.006% to about 0.007%, from about 0.007% to about 0.090%, from about 0.007% to about 0.080%, from about 0.007% to about 0.070%, from about 0.007% to about 0.060%, from about 0.007% to about 0.050%, from about 0.007% to about 0.040%, from about 0.007% to about 0.030%, from about 0.007% to about 0.020%, from about 0.007% to about 0.012%, from about 0.007% to about 0.011%, from about 0.007% to about 0.010%, from about 0.007% to about 0.009%, from about 0.007% to about 0.008%, from about 0.008% to about 0.090%, from about 0.008% to about 0.080%, from about 0.008% to about 0.070%, from about 0.008% to about 0.060%, from about 0.008% to about 0.050%, from about 0.008% to about 0.040%, from about 0.008% to about 0.030%, from about 0.008% to about 0.020%, from about 0.008% to about 0.012%, from about 0.008% to about 0.011%, from about 0.008% to about 0.010%, from about 0.008% to about 0.009%, from about 0.009% to about 0.090%, from about 0.009% to about 0.080%, from about 0.009% to about 0.070%, from about 0.009% to about 0.060%, from about 0.009% to about 0.050%, from about 0.009% to about 0.040%, from about 0.009% to about 0.030%, from about 0.009% to about 0.020%, from about 0.009% to about 0.012%, from about 0.009% to about 0.011%, from about 0.009 to about 0.010, from about 0.010% to about 0.090%, from about 0.010% to about 0.080%, from about 0.010% to about 0.070%, from about 0.010% to about 0.060%, from about 0.010% to about 0.050%, from about 0.010% to about 0.040%, from about 0.010% to about 0.030%, from about 0.010% to about 0.020%, from about 0.010 to about 0.012, from about 0.010 to about 0.011, from about 0.011% to about 0.090%, from about 0.011% to about 0.080%, from about 0.011% to about 0.070%, from about 0.011% to about 0.060%, from about 0.011% to about 0.050%, from about 0.011% to about 0.040%, from about 0.011% to about 0.030%, from about 0.011% to about 0.020%, from about 0.011 to about 0.012, from about 0.012% to about 0.090%, from about 0.012% to about 0.080%, from about 0.012% to about 0.070%, from about 0.012% to about 0.060%, from about 0.012% to about 0.050%, from about 0.012% to about 0.040%, from about 0.012% to about 0.030%, from about 0.012% to about 0.020%, from about 0.020% to about 0.090%, from about 0.020% to about 0.080%, from about 0.020% to about 0.070%, from about 0.020% to about 0.060%, from about 0.020% to about 0.050%, from about 0.020% to about 0.040%, from about 0.020% to about 0.030%, from about 0.030% to about 0.090%, from about 0.030% to about 0.080%, from about 0.030% to about 0.070%, from about 0.030% to about 0.060%, from about 0.030% to about 0.050%, from about 0.030% to about 0.040%, from about 0.040% to about 0.090%, from about 0.040% to about 0.080%, from about 0.040% to about 0.070%, from about 0.040% to about 0.060%, from about 0.040% to about 0.050%, from about 0.050% to about 0.090%, from about 0.050% to about 0.080%, from about 0.050% to about 0.070%, from about 0.050% to about 0.060%, from about 0.060% to about 0.090%, from about 0.060% to about 0.080%, from about 0.060% to about 0.070%, from about 0.070% to about 0.090%, from about 0.070% to about 0.080%, from about 0.080% to about 0.090%, or at about 0.001%, about 0.003%, about 0.005%, about 0.006%, about 0.007%, about 0.008%, about 0.009%, about 0.010%, about 0.011%, about 0.012%, about 0.020%, about 0.030%, about 0.040%, about 0.050%, about 0.060%, about 0.070%, about 0.080%, about 0.090%. In all of these embodiments, the percentile numbers are determined by weight (w/w). Alternatively, in all of these embodiments, the percentile numbers are determined by volume (w/v).

In some embodiments of ophthalmic pharmaceutical compositions, ketorolac or a pharmaceutically acceptable salt thereof (e.g., ketorolac tromethamine) may be present in the amount of from about 0.01% to about 0.6%, from about 0.01% to about 0.5%, from about 0.01% to about 0.4%, from about 0.01% to about 0.3%, from about 0.01% to about 0.2%, from about 0.01% to about 0.1%, from about 0.01% to about 0.05%, from about 0.05% to about 0.6%, from about 0.05% to about 0.5%, from about 0.05% to about 0.4%, from about 0.05% to about 0.3%, from about 0.05% to about 0.2%, from about 0.05% to about 0.1%, from about 0.1% to about 0.6%, from about 0.1% to about 0.5%, from about 0.1% to about 0.4%, from about 0.1% to about 0.3%, from about 0.1% to about 0.2%, from about 0.2% to about 0.6%, from about 0.2% to about 0.5%, from about 0.2% to about 0.4%, from about 0.2% to about 0.3%, from about 0.3% to about 0.6%, from about 0.3% to about 0.5%, from about 0.3% to about 0.4%, from about 0.4% to about 0.6%, from about 0.4% to about 0.5%, from about 0.5% to about 0.6%, or at about 0.01%, about 0.05%, about 0.1%, about 0.2%, about 0.3%, about 0.4%, about 0.5%, about 0.6%. In all of these embodiments, the percentile numbers are determined by weight (w/w). Alternatively, in all of these embodiments, the percentile numbers are determined by volume (w/v).

In some embodiments, an ophthalmic pharmaceutical composition may further comprise a lubricating agent. In general, the lubricating agent may facilitate administration of the ophthalmic pharmaceutical composition to a subject. Suitable lubricants can be independently selected from hyaluronic acid or a pharmaceutically acceptable salt thereof, cellulose or its derivative, carboxymethyl cellulose sodium, hydroxyethyl cellulose, hydroxypropyl methylcellulose, methylcellulose, dextran, gelatin, a polyol, glycerin, polyethylene glycol 300, polyethylene glycol 400, polysorbate, propylene glycol, polyvinyl alcohol, povidone, or mixtures thereof. In some embodiments, an ophthalmic pharmaceutical composition further comprises sodium hyaluronate. In some embodiments, an ophthalmic pharmaceutical composition further comprises hydroxypropyl methylcellulose. In some embodiments, an ophthalmic pharmaceutical composition further comprises sodium hyaluronate and hydroxypropyl methylcellulose. Alternatively, an ophthalmic pharmaceutical composition may not comprise a lubricating agent.

In some embodiments of ophthalmic pharmaceutical compositions, the lubricating agent is sodium hyaluronate, which may be present in the amount of from about 0.01% to about 0.9%, from about 0.01% to about 0.8%, from about 0.01% to about 0.7%, from about 0.01% to about 0.6%, from about 0.01% to about 0.5%, from about 0.01% to about 0.4%, from about 0.01% to about 0.3%, from about 0.01% to about 0.2%, from about 0.01% to about 0.1%, from about 0.01% to about 0.05%, from about 0.05% to about 0.9%, from about 0.05% to about 0.8%, from about 0.05% to about 0.7%, from about 0.05% to about 0.6%, from about 0.05% to about 0.5%, from about 0.05% to about 0.4%, from about 0.05% to about 0.3%, from about 0.05% to about 0.2%, from about 0.05% to about 0.1%, from about 0.1% to about 0.9%, from about 0.1% to about 0.8%, from about 0.1% to about 0.7%, from about 0.1% to about 0.6%, from about 0.1% to about 0.5%, from about 0.1% to about 0.4%, from about 0.1% to about 0.3%, from about 0.1% to about 0.2%, from about 0.2% to about 0.9%, from about 0.2% to about 0.8%, from about 0.2% to about 0.7%, from about 0.2% to about 0.6%, from about 0.2% to about 0.5%, from about 0.2% to about 0.4%, from about 0.2% to about 0.3%, from about 0.3% to about 0.9%, from about 0.3% to about 0.8%, from about 0.3% to about 0.7%, from about 0.3% to about 0.6%, from about 0.3% to about 0.5%, from about 0.3% to about 0.4%, from about 0.4% to about 0.9%, from about 0.4% to about 0.8%, from about 0.4% to about 0.7%, from about 0.4% to about 0.6%, from about 0.4% to about 0.5%, from about 0.5% to about 0.9%, from about 0.5% to about 0.8%, from about 0.5% to about 0.7%, from about 0.5% to about 0.6%, from about 0.6% to about 0.9%, from about 0.6% to about 0.8%, from about 0.6% to about 0.7%, from about 0.7% to about 0.9%, from about 0.7% to about 0.8%, from about 0.8% to about 0.9%, or at about 0.01%, about 0.05%, about 0.1%, about 0.2%, about 0.3%, about 0.4%, about 0.5%, about 0.6%, about 0.7%, about 0.8%, about 0.9%. In all of these embodiments, the percentile numbers are determined by weight (w/w). Alternatively, in all of these embodiments, the percentile numbers are determined by volume (w/v).

In some embodiments of ophthalmic pharmaceutical compositions, the lubricating agent is hydroxypropyl methylcellulose, which may be present in the amount of from about 0.1% to about 2.0%, from about 0.1% to about 1.8%, from about 0.1% to about 1.6%, from about 0.1% to about 1.4%, from about 0.1% to about 1.2%, from about 0.1% to about 1.0%, from about 0.1% to about 0.8%, from about 0.1% to about 0.6%, from about 0.1% to about 0.4%, from about 0.1% to about 0.2%, about 0.2% to about 2.0%, from about 0.2% to about 1.8%, from about 0.2% to about 1.6%, from about 0.2% to about 1.4%, from about 0.2% to about 1.2%, from about 0.2% to about 1.0%, from about 0.2% to about 0.8%, from about 0.2% to about 0.6%, from about 0.2% to about 0.4%, from about 0.4% to about 2.0%, from about 0.4% to about 1.8%, from about 0.4% to about 1.6%, from about 0.4% to about 1.4%, from about 0.4% to about 1.2%, from about 0.4% to about 1.0%, from about 0.4% to about 0.8%, from about 0.4% to about 0.6%, from about 0.6% to about 2.0%, from about 0.6% to about 1.8%, from about 0.6% to about 1.6%, from about 0.6% to about 1.4%, from about 0.6% to about 1.2%, from about 0.6% to about 1.0%, from about 0.6% to about 0.8%, from about 0.8% to about 2.0%, from about 0.8% to about 1.8%, from about 0.8% to about 1.6%, from about 0.8% to about 1.4%, from about 0.8% to about 1.2%, from about 0.8% to about 1.0%, from about 1.0% to about 2.0%, from about 1.0% to about 1.8%, from about 1.0% to about 1.6%, from about 1.0% to about 1.4%, from about 1% to about 1.2%, from about 1.2% to about 2.0%, from about 1.2% to about 1.8%, from about 1.2% to about 1.6%, from about 1.2% to about 1.4%, from about 1.4% to about 2.0%, from about 1.4% to about 1.8%, from about 1.4% to about 1.6%, from about 1.6% to about 2.0%, from about 1.6% to about 1.8%, from about 1.8% to about 2.0%, or at about 0.1%, about 0.2%, about 0.4%, about 0.6%, about 0.8%, about 1.0%, about 1.2%, about 1.4%, about 1.6%, about 1.8%, about 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.01% to 0.4%, diclofenac sodium at a concentration of 0.001% to 0.090%, and sodium hyaluronate at a concentration of 0.01% to 0.9%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.01% to 0.4%, diclofenac sodium at a concentration of 0.001% to 0.090%, and hydroxypropyl methylcellulose at a concentration of 0.1%, to 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.01% to 0.4%, diclofenac sodium at a concentration of 0.001% to 0.090%, sodium hyaluronate at a concentration of 0.01% to 0.9%, and hydroxypropyl methylcellulose at a concentration of 0.1%, to 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.01% to 0.4%, ketorolac tromethamine at a concentration of 0.01% to 0.60%, and sodium hyaluronate at a concentration of 0.01% to 0.9%. In all of these embodiments, the percentile numbers are determined by weight (w/w). Alternatively, in all of these embodiments, the percentile numbers are determined by volume (w/v)

In some embodiments, an ophthalmic pharmaceutical composition comprises pilocarpine hydrochloride or pilocarpine nitrate at a concentration of 0.01% to 0.4%, ketorolac tromethamine at a concentration of 0.01% to 0.60%, and hydroxypropyl methylcellulose at a concentration of 0.1% to 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.01% to 0.4%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.01%. In some embodiments, the ophthalmic pharmaceutical composition comprising pilocarpine hydrochloride or pilocarpine nitrate at a concentration of 0.01% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.01% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.01% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.01% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.01% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.01% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.01% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.01% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.05%. In some embodiments, the ophthalmic pharmaceutical composition comprising pilocarpine hydrochloride or pilocarpine nitrate at a concentration of 0.05% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.05% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.05% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.05% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.05% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.05% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.05% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.05% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.1%. In some embodiments, the ophthalmic pharmaceutical composition comprising pilocarpine hydrochloride or pilocarpine nitrate at a concentration of 0.1% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.1% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.1% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.1% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.1%, further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.1% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.1% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.1% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.15%. In some embodiments, the ophthalmic pharmaceutical composition comprising pilocarpine hydrochloride or pilocarpine nitrate at a concentration of 0.15% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.15% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.15% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.15% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.15% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.15% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.15% further comprises ketorolac tromethamine ata concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.15% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.2%. In some embodiments, the ophthalmic pharmaceutical composition comprising pilocarpine hydrochloride or pilocarpine nitrate at a concentration of 0.2% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.2% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.2% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.2% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.2% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.2% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.2% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.2% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.25%. In some embodiments, the ophthalmic pharmaceutical composition comprising pilocarpine hydrochloride or pilocarpine nitrate at a concentration of 0.25% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.25% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.25% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.25% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.25% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.25% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.25% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.25% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.3%. In some embodiments, the ophthalmic pharmaceutical composition comprising pilocarpine hydrochloride or pilocarpine nitrate at a concentration of 0.3% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.3% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.3% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.3% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.3% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.3%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.3% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.3% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.3% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.35%. In some embodiments, the ophthalmic pharmaceutical composition comprising pilocarpine hydrochloride or pilocarpine nitrate at a concentration of 0.35% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.35% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.35% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.35% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.35% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.3%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.35% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.35% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.35% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

In some embodiments, an ophthalmic pharmaceutical composition comprises pilocarpine hydrochloride or pilocarpine nitrate at a concentration of 0.4%. In some embodiments, the ophthalmic pharmaceutical composition comprising pilocarpine hydrochloride or pilocarpine nitrate at a concentration of 0.4% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%. In some embodiments, the ophthalmic pharmaceutical composition comprising pilocarpine hydrochloride or pilocarpine nitrate at a concentration of 0.4% further comprises ketorolac tromethamine at a concentration of 0.01%, 0.05%, 0.1%, 0.2%, 0.3%, 0.4%, 0.5%, or 0.6%. In some embodiments, the ophthalmic pharmaceutical composition comprising pilocarpine hydrochloride or pilocarpine nitrate at a concentration of 0.4% further comprises sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.4% further comprises hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.4% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise sodium hyaluronate at a concentration of 0.3%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.4% further comprises diclofenac sodium at a concentration of 0.001%, 0.003%, 0.005%, 0.006%, 0.007%, 0.008%, 0.009%, 0.010%, 0.011%, 0.012%, 0.020%, 0.030%, 0.040%, 0.050%, 0.060%, 0.070%, 0.080%, or 0.090%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In some embodiments, the ophthalmic pharmaceutical composition comprising pilocarpine hydrochloride or pilocarpine nitrate at a concentration of 0.4% further comprises ketorolac tromethamine at a concentration of 0.01%, 0.05%, 0.1%, 0.2%, 0.3%, 0.4%, 0.5%, or 0.6%, and may optionally further comprise sodium hyaluronate at a concentration of 0.01%, 0.05%, 0.1%, 0.2%, 0.3%, 0.4%, 0.5%, 0.6%, 0.7%, 0.8%, or 0.9%. In some embodiments, the ophthalmic pharmaceutical composition comprising pilocarpine hydrochloride or pilocarpine nitrate at a concentration of 0.4% further comprises ketorolac tromethamine at a concentration of 0.01%, 0.05%, 0.1%, 0.2%, 0.3%, 0.4%, 0.5%, or 0.6%, and may optionally further comprise hydroxypropyl methylcellulose at a concentration of 0.1%, 0.2%, 0.4%, 0.6%, 0.8%, 1.0%, 1.2%, 1.4%, 1.6%, 1.8%, or 2.0%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.01% and diclofenac sodium at a concentration of from 0.001% to 0.012%. In some embodiments, an ophthalmic pharmaceutical composition comprises pilocarpine hydrochloride or pilocarpine nitrate at a concentration of 0.01% and ketorolac tromethamine at a concentration of from 0.01% to 0.50%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.05% and diclofenac sodium at a concentration of from 0.001% to 0.012%. In some embodiments, an ophthalmic pharmaceutical composition comprises pilocarpine hydrochloride or pilocarpine nitrate at a concentration of 0.05% and ketorolac tromethamine at a concentration of from 0.01% to 0.50%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.1%, and diclofenac sodium at a concentration of from 0.001% to 0.012%. In some embodiments, an ophthalmic pharmaceutical composition comprises pilocarpine hydrochloride or pilocarpine nitrate at a concentration of 0.1% and ketorolac tromethamine at a concentration of from 0.01% to 0.50%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.15% and diclofenac sodium at a concentration of from 0.001% to 0.012%. In some embodiments, an ophthalmic pharmaceutical composition comprises pilocarpine hydrochloride or pilocarpine nitrate at a concentration of 0.15% and ketorolac tromethamine at a concentration of from 0.01% to 0.50%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.2% and diclofenac sodium at a concentration of from 0.001% to 0.012%. In some embodiments, an ophthalmic pharmaceutical composition comprises pilocarpine hydrochloride or pilocarpine nitrate at a concentration of 0.2% and ketorolac tromethamine at a concentration of from 0.01% to 0.50%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.01% and sodium hyaluronate at a concentration of from 0.01% to 0.2%. In some embodiments, an ophthalmic pharmaceutical composition comprises pilocarpine hydrochloride or pilocarpine nitrate at a concentration of 0.01% and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.01%, sodium hyaluronate at a concentration of from 0.01% to 0.2%, and hydroxypropyl methylcellulose at a concentration of from 0.1%, to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.05% and sodium hyaluronate at a concentration of from 0.01% to 0.2%. In some embodiments, an ophthalmic pharmaceutical composition comprises pilocarpine hydrochloride or pilocarpine nitrate at a concentration of 0.05% and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.05%, sodium hyaluronate at a concentration of from 0.01% to 0.2%, and hydroxypropyl methylcellulose at a concentration of from 0.1%, to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.1%, and sodium hyaluronate at a concentration of from 0.01% to 0.2%. In some embodiments, an ophthalmic pharmaceutical composition comprises pilocarpine hydrochloride or pilocarpine nitrate at a concentration of 0.1% and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.1%, sodium hyaluronate at a concentration of from 0.01% to 0.2%, and hydroxypropyl methylcellulose at a concentration of from 0.1%, to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.15% and sodium hyaluronate at a concentration of from 0.01% to 0.2%. In some embodiments, an ophthalmic pharmaceutical composition comprises pilocarpine hydrochloride or pilocarpine nitrate at a concentration of 0.15% and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.15%, sodium hyaluronate at a concentration of from 0.01% to 0.2%, and hydroxypropyl methylcellulose at a concentration of from 0.1%, to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.2% and sodium hyaluronate at a concentration of from 0.01% to 0.2%. In some embodiments, an ophthalmic pharmaceutical composition comprises pilocarpine hydrochloride or pilocarpine nitrate at a concentration of 0.2% and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.2%, sodium hyaluronate at a concentration of from 0.01% to 0.2%, and hydroxypropyl methylcellulose at a concentration of from 0.1%, to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.01%, diclofenac sodium at a concentration of from 0.001% to 0.012%, and sodium hyaluronate at a concentration of from 0.01% to 0.2%. In some embodiments, an ophthalmic pharmaceutical composition comprises pilocarpine hydrochloride or pilocarpine nitrate at a concentration of 0.01%, diclofenac sodium at a concentration of from 0.001% to 0.012%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.01%, diclofenac sodium at a concentration of from 0.001% to 0.012%, sodium hyaluronate at a concentration of from 0.01% to 0.2%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.01%, ketorolac tromethamine at a concentration of from 0.01% to 0.50%, and sodium hyaluronate at a concentration of from 0.01% to 0.2%. In some embodiments, an ophthalmic pharmaceutical composition comprises pilocarpine hydrochloride or pilocarpine nitrate at a concentration of 0.01%, ketorolac tromethamine at a concentration of from 0.01% to 0.50%, and hydroxypropyl methylcellulose at a concentration of from 0.1% to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.05%, diclofenac sodium at a concentration of from 0.001% to 0.012%, and sodium hyaluronate at a concentration of from 0.01% to 0.2%. In some embodiments, an ophthalmic pharmaceutical composition comprises pilocarpine hydrochloride or pilocarpine nitrate at a concentration of 0.05%, diclofenac sodium at a concentration of from 0.001% to 0.012%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.05%, diclofenac sodium at a concentration of from 0.001% to 0.012%, sodium hyaluronate at a concentration of from 0.01% to 0.2%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.05%, ketorolac tromethamine at a concentration of from 0.01% to 0.50%, and sodium hyaluronate at a concentration of from 0.01% to 0.2%. In some embodiments, an ophthalmic pharmaceutical composition comprises pilocarpine hydrochloride or pilocarpine nitrate at a concentration of 0.05%, ketorolac tromethamine at a concentration of from 0.01% to 0.50%, and hydroxypropyl methylcellulose at a concentration of from 0.1% to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.10%, diclofenac sodium at a concentration of from 0.001% to 0.012%, and sodium hyaluronate at a concentration of from 0.01% to 0.2%. In some embodiments, an ophthalmic pharmaceutical composition comprises pilocarpine hydrochloride or pilocarpine nitrate at a concentration of 0.10%, diclofenac sodium at a concentration of from 0.001% to 0.012%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.10%, diclofenac sodium at a concentration of from 0.001% to 0.012%, sodium hyaluronate at a concentration of from 0.01% to 0.2%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.10%, ketorolac tromethamine at a concentration of from 0.01% to 0.50%, and sodium hyaluronate at a concentration of from 0.01% to 0.2%. In some embodiments, an ophthalmic pharmaceutical composition comprises pilocarpine hydrochloride or pilocarpine nitrate at a concentration of 0.10%, ketorolac tromethamine at a concentration of from 0.01% to 0.50%, and hydroxypropyl methylcellulose at a concentration of from 0.1% to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.15%, diclofenac sodium at a concentration of from 0.001% to 0.012%, and sodium hyaluronate at a concentration of from 0.01% to 0.2%. In some embodiments, an ophthalmic pharmaceutical composition comprises pilocarpine hydrochloride or pilocarpine nitrate at a concentration of 0.15%, diclofenac sodium at a concentration of from 0.001% to 0.012%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.15%, diclofenac sodium at a concentration of from 0.001% to 0.012%, sodium hyaluronate at a concentration of from 0.01% to 0.2%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.15%, ketorolac tromethamine at a concentration of from 0.01% to 0.50%, and sodium hyaluronate at a concentration of from 0.01% to 0.2%. In some embodiments, an ophthalmic pharmaceutical composition comprises pilocarpine hydrochloride or pilocarpine nitrate at a concentration of 0.15%, ketorolac tromethamine at a concentration of from 0.01% to 0.50%, and hydroxypropyl methylcellulose at a concentration of from 0.1% to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition comprises pilocarpine hydrochloride or pilocarpine nitrate at a concentration of 0.2%, diclofenac sodium at a concentration of from 0.001% to 0.012%, and sodium hyaluronate at a concentration of from 0.01% to 0.2%. In some embodiments, an ophthalmic pharmaceutical composition comprises pilocarpine hydrochloride or pilocarpine nitrate at a concentration of 0.2%, diclofenac sodium at a concentration of from 0.001% to 0.012%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.2%, diclofenac sodium at a concentration of from 0.001% to 0.012%, sodium hyaluronate at a concentration of from 0.01% to 0.2%, and hydroxypropyl methylcellulose at a concentration of from 0.1% to 1.2%. In some embodiments, an ophthalmic pharmaceutical composition comprises pilocarpine hydrochloride or pilocarpine nitrate at a concentration of 0.2%, ketorolac tromethamine at a concentration of from 0.01% to 0.50%, and sodium hyaluronate at a concentration of from 0.01% to 0.2%. In some embodiments, an ophthalmic pharmaceutical composition comprises pilocarpine hydrochloride or pilocarpine nitrate at a concentration of 0.2%, ketorolac tromethamine at a concentration of from 0.01% to 0.50%, and hydroxypropyl methylcellulose at a concentration of from 0.1% to 1.2%. In all of these embodiments, the percentile numbers are determined by weight (w/w). Alternatively, in all of these embodiments, the percentile numbers are determined by volume (w/v).

For example, in some embodiments, an ophthalmic pharmaceutical composition can be any one of the following non-limiting examples of compositions that comprise the components listed in the table in this paragraph and a pharmaceutically acceptable carrier. In some embodiments, an ophthalmic pharmaceutical can be any one of the following non-limiting examples of compositions that comprise the components listed in the table in this paragraph and a pharmaceutically acceptable carrier, further comprising hydroxypropyl methylcellulose at a concentration of from about 0.1% to about 1.2%. In some embodiments, an ophthalmic pharmaceutical can be any one of the following non-limiting examples of compositions that comprise the components listed in the table in this paragraph and a pharmaceutically acceptable carrier, further comprising hydroxypropyl methylcellulose at a concentration of about 0.1%, about 0.8%, or about 1.2%. In all of these compositions, the percentile numbers are determined by weight (w/w). Alternatively, in all of these embodiments, the percentile numbers are determined by volume (w/v).

| Composition | pilocarpine hydrochloride or pilocarpine nitrate | diclofenac sodium | sodium hyaluronate |
|---|---|---|---|
| 1 | 0.1% | 0% | 0% |
| 2 | 0.1% | 0.001% | 0% |
| 3 | 0.1% | 0.006% | 0% |
| 4 | 0.1% | 0.090% | 0% |
| 5 | 0.1% | 0% | 0.01% |
| 6 | 0.1% | 0% | 0.1% |
| 7 | 0.1% | 0% | 0.9% |
| 8 | 0.1% | 0.001% | 0.01% |
| 9 | 0.1% | 0.001% | 0.1% |
| 10 | 0.1% | 0.001% | 0.9% |
| 11 | 0.1% | 0.006% | 0.01% |
| 12 | 0.1% | 0.006% | 0.1% |
| 13 | 0.1% | 0.006% | 0.9% |
| 14 | 0.1% | 0.090% | 0.01% |
| 15 | 0.1% | 0.090% | 0.1% |
| 16 | 0.1% | 0.090% | 0.9% |
| 17 | 0.2% | 0% | 0% |
| 18 | 0.2% | 0.001% | 0% |
| 19 | 0.2% | 0.006% | 0% |
| 20 | 0.2% | 0.090% | 0% |
| 21 | 0.2% | 0% | 0.01% |
| 22 | 0.2% | 0% | 0.1% |
| 23 | 0.2% | 0% | 0.9% |
| 24 | 0.2% | 0.001% | 0.01% |
| 25 | 0.2% | 0.001% | 0.1% |
| 26 | 0.2% | 0.001% | 0.9% |
| 27 | 0.2% | 0.006% | 0.01% |
| 28 | 0.2% | 0.006% | 0.1% |
| 29 | 0.2% | 0.006% | 0.9% |
| 30 | 0.2% | 0.090% | 0.01% |
| 31 | 0.2% | 0.090% | 0.1% |
| 32 | 0.2% | 0.090% | 0.9% |

For example, in some embodiments, an ophthalmic pharmaceutical composition can be any one of the following non-limiting examples of compositions that comprise the components listed in the table in this paragraph and a pharmaceutically acceptable carrier. In all of these compositions, the percentile numbers are determined by weight (w/w). Alternatively, in all of these embodiments, the percentile numbers are determined by volume (w/v).

| Composition | pilocarpine hydrochloride or pilocarpine nitrate | diclofenac sodium | hydroxypropyl methylcellulose |
|---|---|---|---|
| 33 | 0.1% | 0% | 0% |
| 34 | 0.1% | 0.001% | 0% |
| 35 | 0.1% | 0.006% | 0% |
| 36 | 0.1% | 0.090% | 0% |
| 37 | 0.1% | 0% | 0.1% |
| 38 | 0.1% | 0% | 0.8% |
| 39 | 0.1% | 0% | 1.2% |
| 40 | 0.1% | 0.001% | 0.1% |
| 41 | 0.1% | 0.001% | 0.8% |
| 42 | 0.1% | 0.001% | 1.2% |
| 43 | 0.1% | 0.006% | 0.1% |
| 44 | 0.1% | 0.006% | 0.8% |
| 45 | 0.1% | 0.006% | 1.2% |
| 46 | 0.1% | 0.090% | 0.1% |
| 47 | 0.1% | 0.090% | 0.8% |
| 48 | 0.1% | 0.090% | 1.2% |
| 49 | 0.2% | 0% | 0% |
| 50 | 0.2% | 0.001% | 0% |
| 51 | 0.2% | 0.006% | 0% |
| 52 | 0.2% | 0.090% | 0% |
| 53 | 0.2% | 0% | 0.1% |
| 54 | 0.2% | 0% | 0.8% |
| 55 | 0.2% | 0% | 1.2% |
| 56 | 0.2% | 0.001% | 0.1% |
| 57 | 0.2% | 0.001% | 0.8% |
| 58 | 0.2% | 0.001% | 1.2% |
| 59 | 0.2% | 0.006% | 0.1% |
| 60 | 0.2% | 0.006% | 0.8% |
| 61 | 0.2% | 0.006% | 1.2% |
| 62 | 0.2% | 0.090% | 0.1% |
| 63 | 0.2% | 0.090% | 0.8% |
| 64 | 0.2% | 0.090% | 1.2% |

For example, in some embodiments, an ophthalmic pharmaceutical composition can be any one of the following non-limiting examples of compositions that comprise the components listed in the table in this paragraph and a pharmaceutically acceptable carrier. In all of these compositions, the percentile numbers are determined by weight (w/w). Alternatively, in all of these embodiments, the percentile numbers are determined by volume (w/v).

| Composition | pilocarpine hydrochloride or pilocarpine nitrate | ketorolac tromethamine | sodium hyaluronate |
|---|---|---|---|
| 65 | 0.1% | 0% | 0% |
| 66 | 0.1% | 0.01% | 0% |
| 67 | 0.1% | 0.30% | 0% |
| 68 | 0.1% | 0.50% | 0% |
| 69 | 0.1% | 0% | 0.01% |
| 70 | 0.1% | 0% | 0.1% |
| 71 | 0.1% | 0% | 0.9% |
| 72 | 0.1% | 0.01% | 0.01% |
| 73 | 0.1% | 0.01% | 0.1% |
| 74 | 0.1% | 0.01% | 0.9% |
| 75 | 0.1% | 0.30% | 0.01% |
| 76 | 0.1% | 0.30% | 0.1% |
| 77 | 0.1% | 0.30% | 0.9% |
| 78 | 0.1% | 0.50% | 0.01% |
| 79 | 0.1% | 0.50% | 0.1% |
| 80 | 0.1% | 0.50% | 0.9% |
| 81 | 0.2% | 0% | 0% |
| 82 | 0.2% | 0.01% | 0% |
| 83 | 0.2% | 0.30% | 0% |
| 84 | 0.2% | 0.50% | 0% |
| 85 | 0.2% | 0% | 0.01% |
| 86 | 0.2% | 0% | 0.1% |
| 87 | 0.2% | 0% | 0.9% |
| 88 | 0.2% | 0.01% | 0.01% |
| 89 | 0.2% | 0.01% | 0.1% |
| 90 | 0.2% | 0.01% | 0.9% |
| 91 | 0.2% | 0.30% | 0.01% |
| 92 | 0.2% | 0.30% | 0.1% |
| 93 | 0.2% | 0.30% | 0.9% |
| 94 | 0.2% | 0.50% | 0.01% |
| 95 | 0.2% | 0.50% | 0.1% |
| 96 | 0.2% | 0.50% | 0.9% |

For example, in some embodiments, an ophthalmic pharmaceutical composition can be any one of the following non-limiting examples of compositions that comprise the components listed in the table in this paragraph and a pharmaceutically acceptable carrier. In all of these compositions, the percentile numbers are determined by weight (w/w). Alternatively, in all of these embodiments, the percentile numbers are determined by volume (w/v).

| Composition | pilocarpine hydrochloride or pilocarpine nitrate | ketorolac tromethamine | hydroxypropyl methylcellulose |
|---|---|---|---|
| 97 | 0.1% | 0% | 0% |
| 98 | 0.1% | 0.01% | 0% |
| 99 | 0.1% | 0.30% | 0% |
| 100 | 0.1% | 0.50% | 0% |
| 101 | 0.1% | 0% | 0.1% |
| 102 | 0.1% | 0% | 0.8% |
| 103 | 0.1% | 0% | 1.2% |
| 104 | 0.1% | 0.01% | 0.1% |
| 105 | 0.1% | 0.01% | 0.8% |
| 106 | 0.1% | 0.01% | 1.2% |
| 107 | 0.1% | 0.30% | 0.1% |
| 108 | 0.1% | 0.30% | 0.8% |
| 109 | 0.1% | 0.30% | 1.2% |
| 110 | 0.1% | 0.50% | 0.1% |
| 111 | 0.1% | 0.50% | 0.8% |
| 112 | 0.1% | 0.50% | 1.2% |
| 113 | 0.2% | 0% | 0% |
| 114 | 0.2% | 0.01% | 0% |
| 115 | 0.2% | 0.30% | 0% |
| 116 | 0.2% | 0.50% | 0% |
| 117 | 0.2% | 0% | 0.1% |
| 118 | 0.2% | 0% | 0.8% |
| 119 | 0.2% | 0% | 1.2% |
| 120 | 0.2% | 0.01% | 0.1% |
| 121 | 0.2% | 0.01% | 0.8% |
| 122 | 0.2% | 0.01% | 1.2% |
| 123 | 0.2% | 0.30% | 0.1% |
| 124 | 0.2% | 0.30% | 0.8% |
| 125 | 0.2% | 0.30% | 1.2% |
| 126 | 0.2% | 0.50% | 0.1% |
| 127 | 0.2% | 0.50% | 0.8% |
| 128 | 0.2% | 0.50% | 1.2% |

In some embodiments, an ophthalmic pharmaceutical composition can comprises a pharmaceutically acceptable carrier and either one, two, three, or four of the components selected from (1) pilocarpine hydrochloride or pilocarpine nitrate; (2) diclofenac sodium; (3) sodium hyaluronate; and (4) hydroxypropyl methylcellulose, wherein the pilocarpine hydrochloride or pilocarpine nitrate is at a concentration of from about 0.01% to about 0.4%, diclofenac sodium is at a concentration of from about 0.001% to about 0.090%, sodium hyaluronate is at a concentration of from about 0.01% to about 0.9%, and/or hydroxypropyl methylcellulose is at a concentration of from about 0.1% to about 2.0%. In all of these compositions, the percentile numbers are determined by weight (w/w). Alternatively, in all of these embodiments, the percentile numbers are determined by volume (w/v).

In some embodiments, an ophthalmic pharmaceutical composition according to this disclosure may further comprise an ophthalmically acceptable carrier, which, as used herein, includes, but is not limited to, solvent, dispersion media, diluent, dispersion, suspension aid, surface active agent, isotonic agent, thickening or emulsifying agent, preservative, core-shell nanoparticles, polymer, peptide, protein, cell, hyaluronidase, and mixtures thereof. The use of such media and agents that are compatible with ophthalmic administration is well known in the art. Various carriers for formulating ophthalmic pharmaceutical compositions and techniques for preparing the composition are well known in the art (see, e.g., Remington: The Science and Practice of Pharmacy, 22nd Edition, Edited by Allen, Loyd V., Jr, Pharmaceutical Press; incorporated herein by reference in its entirety). For example, in some embodiments, an ophthalmic pharmaceutical composition according to this disclosure may comprise one or more preservatives such as phenol, cresol, p-aminobenzoic acid, BDSA, sorbitrate, chlorhexidine, benzalkonium chloride, sorbic acid, Purite®. (oxychloride compounds), Polyquad®. (quaternary ammonium), polyhexamethylene biguanide, sodium perborate, and the like. In some embodiments, ophthalmic pharmaceutical compositions intended for long-term use in chronic conditions can be formulated and packaged to minimize or eliminate the use of preservatives that may irritate the eye. For example, the ophthalmic pharmaceutical composition may be packaged in single-dose containers, or in containers utilizing alternative means for minimizing microbial contamination, such as membranes, valve mechanisms, or silver.

In some embodiments, an ophthalmic pharmaceutical composition further comprises an isotonic agent, a wetting agent, a buffer, a stabilizer, a pH agent, a solubilizer, a thickening agent, and/or a dispersing agent. These agents are well known to those skilled in the ophthalmic art (see, e.g., U.S. Pat. Nos. 8,299,079 and 8,524,758). For example, the pharmaceutical compositions may contain a tonicity agent to adjust the preparation to the desired isotonic range. Some examples of the tonicity agents include glycerin, mannitol, sorbitol, and sodium chloride. Additionally or alternatively, the pharmaceutical compositions may contain a wetting agent that reduces the surface tension of water or another liquid, causing the liquid to spread across or penetrate more easily the surface of a solid. Some examples of the wetting agents in ophthalmic compositions include carboxymethylcellulose, hydroxypropyl methylcellulose, glycerin, mannitol, polyvinyl alcohol or hydroxyethylcellulose. Additionally or alternatively, the pharmaceutical compositions may contain a buffering agent to maintain the pH in the therapeutically useful range. Buffering agents used are those known to those skilled in the art, and, while not intending to be limiting, some examples are acetate, borate, carbonate, citrate, and phosphate buffers. Additionally or alternatively, the pharmaceutical compositions may contain one or more stabilizers, such as sodium hydrogen sulphite, ethylenediaminetetraacetic acids, and the like. Additionally or alternatively, the pharmaceutical compositions may contain one or more solubilizers, such as polysorbate, polyethylene glycol, propylene glycol, macrogol 4000, and the like. Additionally or alternatively, the pharmaceutical compositions may contain one or more thickeners that make the preparation of the present disclosure dense or viscous in consistency. Suitable thickeners include, for example, non-ionic water-soluble polymers, fatty alcohols, fatty acids, anionic polymers, and their alkali salts and mixtures thereof. Additionally or alternatively, the pharmaceutical compositions may contain one or more dispersing agents such as poly(ethylene-glycol), polyethoxylated castor oil, alcohol having 12 to 20 carbon atoms, and their mixtures thereof.

In some embodiments, an ophthalmic pharmaceutical composition is a slow release composition. For example, for a slow release ophthalmic pharmaceutical composition, it is known that delivery by way of an intravitreal microinsert near the base of the eye is efficient and advantageous (e.g., WO 2011/079123 A1). The advantage of the microinsert is that the slowly released ingredients remain in the eye and are not lost via the natural drainage channels associated with fluids introduced onto the ocular surface. The microinsert saves the patients time and effort by avoiding repeat instillation of drops every so often.

An ophthalmic pharmaceutical composition according to this disclosure may be in the form of an eye drop formulation. Other forms of application to the eye may be possible. For example, an ophthalmic pharmaceutical according to this disclosure may be in the form of a suspension. In some embodiments, an ophthalmic pharmaceutical according to this disclosure may be in the form of a gel. In some embodiments, an ophthalmic pharmaceutical according to this disclosure may be in the form of an eye ointment. In some embodiments, an ophthalmic pharmaceutical according to this disclosure may be in the form of an injectable solution. In some embodiments, an ophthalmic pharmaceutical according to this disclosure may be in the form of an eye spray.

An ophthalmic pharmaceutical composition according to this disclosure may be suitable for topical delivery to a subject's eye or tissue surrounding the eye. An ophthalmic pharmaceutical composition according to this disclosure may be suitable for implantation in or on a subject's eye or tissue surrounding the eye. In some embodiments, the ophthalmic pharmaceutical composition is suitable for implantation into subconjunctival space, naso-lacrimal duct, or vitreous body of the subject.

In some embodiments, an ophthalmic pharmaceutical composition according to this disclosure may be surgically implanted into the subconjunctival space by an ophthalmic surgeon after s/he has decided that the patient would benefit from the implant following preliminary testing using the topical drops. The constituents passively reach the iris and interact with the muscle fibers of the iris changing the size of the pupil. This action leads to an increase in depth of field and improvement in the distance and near vision as discussed in this disclosure.

Treating Subjects Suffering from the Symptoms of Presbyopia

It is an aim of the present disclosure to treat subjects suffering from the symptoms of presbyopia by direct administration of a therapeutically effective amount of an ophthalmic pharmaceutical composition according to this disclosure. Administration of an ophthalmic pharmaceutical composition may therefore release or eliminate the symptoms of presbyopia to improve the ability of the patient to focus on objects at a nearby distance, including objects at around a normal reading distance. Administration of an ophthalmic pharmaceutical composition may also cause a significant reduction in discomfort or risk of falls when using progressive or bifocal lenses, and/or diminish or complete relieve blurring and dimness after eye surgery.

The extent of presbyopia after using the ophthalmic pharmaceutical compositions of the present disclosure may be at least 10%, at least 20%, at least 30%, at least 40%, at least 50%, at least 60%, at least 70%, at least 80%, at least 90%, or at least 100% less than the amount of presbyopia that would have been present without using the compositions in this disclosure. The extent of presbyopia may be determined by any method known in the art for ophthalmic examination. For example, standard tests may be performed to examine the ability of the patient to focus on objects at a nearby distance, including objects at around a normal reading distance, after administration of the ophthalmic pharmaceutical compositions of the present disclosure.

In some embodiments, the treatment may correct presbyopia in a subject for about 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, or 1 hour. In some embodiments, the treatment may correct presbyopia in a subject for up to 24 hours.

In some embodiments, the administration of an ophthalmic pharmaceutical composition according to this disclosure corrects presbyopia without adversely affecting night vision. In some embodiments, the administration of an ophthalmic pharmaceutical composition according to this disclosure corrects presbyopia without adversely reducing visual field.

In some embodiments, ophthalmic pharmaceutical compositions according to this disclosure may be used for correcting presbyopia in a subject, wherein the subject
a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

Other aspects of the disclosure relate to delivery systems for administering of an ophthalmic pharmaceutical composition according to this disclosure to a subject in need thereof. In some embodiments, the composition may be administered topically to a subject's eye or tissue surrounding the eye. In some embodiments, the composition may be administered through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, naso-lacrimal duct, or vitreous body of the subject. In some embodiments, the ophthalmic pharmaceutical composition is a slow release composition.

In some embodiments, a method for correcting presbyopia in a subject comprises administering an ophthalmic pharmaceutical composition in the form of an eye drop formulation. In some embodiments, an ophthalmic pharmaceutical composition for correcting presbyopia may be in the form of an eye suspension. In some embodiments, an ophthalmic pharmaceutical composition for correcting presbyopia may be in the form of a gel. In some embodiments, an ophthalmic pharmaceutical composition for correcting presbyopia may be in the form of an ointment. In some embodiments, an ophthalmic pharmaceutical composition for correcting presbyopia may be in the form of an injectable solution. In some embodiments, an ophthalmic pharmaceutical composition for correcting presbyopia may be in the form of an eye spray.

In some embodiments, an ophthalmic pharmaceutical composition is administered to a subject for correcting presbyopia, preferably in one administration. In some embodiments, an ophthalmic pharmaceutical composition is administered to a subject for correcting presbyopia, preferably in multiple (e.g., two, three, four, five, six, seven, eight, nine, ten, eleven, twelve, thirteen, fourteen, fifteen, sixteen, seventeen, eighteen, nineteen, twenty, or more) administrations. In each of the embodiments in this paragraph, the "multiple administrations" can be separated from each other by short (1-5 minutes), medium (6-30 minutes), or long (more than 30 minutes, or even hours) intervals of time.

The ophthalmic pharmaceutical composition may be administered to a subject using any dosage of administration effective for correcting presbyopia. The exact dosage required will vary from subject to subject, depending on the species, age, and general condition of the subject, the severity of the disease, the particular formulation, its mode of administration, its mode of activity, and the like. It will be understood, however, that the total daily usage of the compositions may be decided by the attending ophthalmic physician within the scope of sound medical judgment. The specific pharmaceutically effective, dose level for any particular patient will depend upon a variety of factors including the severity of the presbyopia, the specific composition employed, the age, body weight, general health, sex and diet of the patient, the time of administration, route of administration, the duration of the treatment, and like factors well known in the ophthalmic arts.

However, the present disclosure also encompasses the delivery of ophthalmic pharmaceutical composition for correcting presbyopia, by any appropriate route taking into consideration likely advances in the sciences of drug delivery.

Additional Applications of the Ophthalmic Compositions of the Disclosure

In some embodiments, ophthalmic pharmaceutical compositions according to this disclosure may also be used for treating other health conditions, for example, in a subject with symptoms of presbyopia with no history of eye surgery. In some embodiments, ophthalmic pharmaceutical compositions according to this disclosure may be used in a subject who experiences the following conditions: (a) extreme skin conditions (e.g., tryophobia, ichthyyosis), (b) multiple allergy syndrome, and/or (c) diabetics. In some embodiments, ophthalmic pharmaceutical compositions according to this disclosure may be used in a subject who has received the following kinds of eye surgery: (a) post-cataract implantation with intra-ocular implant lenses, (b) post-laser eye surgery (laser-assisted in situ keratomileusis (LASIK), photo refractive keratectomy (PRK), or analogues thereof), and/or (c) post-implantation of phakic intra-ocular implants. In some embodiments, ophthalmic pharmaceutical compositions according to this disclosure may be used for paediatric cases (e.g., squint in childhood) where eye surgery is not recommended.

Another aspect of the present disclosure relates to the administration of an ophthalmic pharmaceutical composition according this disclosure for modulating several physiological processes in a subject. As non-limiting examples, the modulation of a physiological process can include reducing the size of pupil, inducing miosis, increasing the depth of field, decreasing the magnitude of higher order aberrations, and/or improving uncorrected near and distance visual acuity in a subject.

In some embodiments, a method of reducing the size of pupil in a subject comprising administering to the subject a therapeutically effective amount of an ophthalmic pharmaceutical composition according this disclosure. In some embodiments, the subject a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, a method of reducing the size of pupil in a subject comprising administering to the subject a therapeutically effective amount of an ophthalmic pharmaceutical composition according this disclosure, wherein the ophthalmic pharmaceutical composition is a slow release composition. In some embodiments, the composition may be administered topically to a subject's eye or tissue surrounding the eye. In some embodiments, the composition may be administered through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, naso-lacrimal duct, or vitreous body of the subject. The compositions may be in the form of a suspension, gel, ointment, injectable solution, spray, or eye drop formulation.

In any of the embodiments for reducing the size of pupil in a subject, the effects of the ophthalmic pharmaceutical composition on reducing the size of pupil can be evaluated by methods well-known in the art (see, e.g., Example 1 disclosed herein).

In some embodiments, a method of inducing miosis in a subject comprising administering to the subject a therapeutically effective amount of an ophthalmic pharmaceutical composition according this disclosure. In some embodiments, the subject a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, a method of inducing miosis in a subject comprising administering to the subject a therapeutically effective amount of an ophthalmic pharmaceutical composition according this disclosure, wherein the ophthalmic pharmaceutical composition is a slow release composition. In some embodiments, the composition may be administered topically to a subject's eye or tissue surrounding the eye. In some embodiments, the composition may be administered through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, naso-lacrimal duct, or vitreous body of the subject. The compositions may be in the form of a suspension, gel, ointment, injectable solution, spray, or eye drop formulation.

In any of the embodiments for inducing miosis in a subject, the effects of the ophthalmic pharmaceutical composition on inducing miosis can be evaluated by methods well-known in the art (see, e.g., Example 1 disclosed herein).

In some embodiments, a method of increasing the depth of field in a subject's eye comprising administering to the subject a therapeutically effective amount of an ophthalmic pharmaceutical composition according this disclosure. In some embodiments, the subject a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, a method of increasing the depth of field in a subject's eye comprising administering to the subject a therapeutically effective amount of an ophthalmic pharmaceutical composition according this disclosure, wherein the ophthalmic pharmaceutical composition is a slow release composition. In some embodiments, the composition may be administered topically to a subject's eye or tissue surrounding the eye. In some embodiments, the composition may be administered through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, naso-lacrimal duct, or vitreous body of the subject. The compositions may be in the form of a suspension, gel, ointment, injectable solution, spray, or eye drop formulation.

In any of the embodiments for increasing the depth of field in a subject's eye, the effects of the ophthalmic pharmaceutical composition on increasing the depth of field can be evaluated by methods well-known in the art (see, e.g., Example 1 disclosed herein).

In some embodiments, a method of decreasing the magnitude of higher order aberrations in a subject's eye comprising administering to the subject a therapeutically effective amount of an ophthalmic pharmaceutical composition according this disclosure. In some embodiments, the subject a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, a method of decreasing the magnitude of higher order aberrations in a subject's eye comprising administering to the subject a therapeutically effective amount of an ophthalmic pharmaceutical composition according this disclosure, wherein the ophthalmic pharmaceutical composition is a slow release composition. In some embodiments, the composition may be administered topically to a subject's eye or tissue surrounding the eye. In some embodiments, the composition may be administered through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, nasolacrimal duct, or vitreous body of the subject. The compositions may be in the form of a suspension, gel, ointment, injectable solution, spray, or eye drop formulation.

In any of the embodiments for decreasing the magnitude of higher order aberrations in a subject's eye, the effects of the ophthalmic pharmaceutical composition on decreasing the magnitude of higher order aberrations can be evaluated by methods well-known in the art. For example, non-invasive objective measurements of the $3^{rd}$, $4^{th}$ and $5^{th}$ ocular higher order aberrations (coma, spherical aberration and trefoil) may be conducted every visit using wavefront aberrometry.

In some embodiments, a method of improving uncorrected near and distance visual acuity in a subject comprising administering to the subject a therapeutically effective amount of an ophthalmic pharmaceutical composition according this disclosure. In some embodiments, the subject a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, a method of improving uncorrected near and distance visual acuity in a subject comprising administering to the subject a therapeutically effective amount of an ophthalmic pharmaceutical composition according this disclosure, wherein the ophthalmic pharmaceutical composition is a slow release composition. In some embodiments, the composition may be administered topically to a subject's eye or tissue surrounding the eye. In some embodiments, the composition may be administered through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, naso-lacrimal duct, or vitreous body of the subject. The compositions may be in the form of a suspension, gel, ointment, injectable solution, spray, or eye drop formulation.

In any of the embodiments for improving uncorrected near and distance visual acuity in a subject, the effects of the ophthalmic pharmaceutical composition on improving uncorrected near and distance visual acuity can be evaluated by methods well-known in the art. For example, visual acuity may be assessed at all study visits using a standardized eye chart to determine vision at various distances. The test may be performed on one eye at a time by covering the eye not being tested, and binocularly. Uncorrected visual acuity may be assessed at distance, intermediate (50-80 cm), and near (40 cm). Luminosity measurements for visual acuity may be conducted as follows: distance and intermediate are measured at normal light conditions and recorded by a light meter. Near acuity may be measured both in poor light (room lights dimmed to half normal appearance in consulting room) and bright light (lights on full print illuminated from over left shoulder)—both are also recorded by a light meter. For distance and intermediate, the luminance should be around 3,000 Lux; for near, the luminance should be between 750 and 1,000 Lux for low contrast, and 3,000 Lux for high contrast. All acuity measurements may be recorded in either decimal or LogMar notation. Decimal notation is preferred.

Preparations Comprising Ophthalmic Compositions

Another aspect of the present disclosure relates to different preparations (e.g., implant or kit) comprising an ophthalmic pharmaceutical composition according this disclosure.

Some embodiments relate to an implant comprising an ophthalmic pharmaceutical composition according this disclosure. In some embodiments, the implant may be introduced through surgical intervention in or on a subject's eye or tissue surrounding the eye. In some embodiments, the surgical intervention comprises a step of implanting (e.g., by way of ocular inserts) the ophthalmic pharmaceutical composition in or on the subject's eye or tissue surrounding the eye. In some embodiments, the ophthalmic pharmaceutical composition is implanted into subconjunctival space, nasolacrimal duct, or vitreous body of the subject. In some embodiments, the ophthalmic pharmaceutical composition the ophthalmic pharmaceutical composition is a slow release composition.

It is well known that delivery by way of an intravitreal microinsert near the base of the eye is efficient and advantageous (e.g., WO 2011/079123 A1). The advantage of the microinsert is that the slowly released ingredients remain in the eye and are not lost via the natural drainage channels associated with fluids introduced onto the ocular surface. The microinsert saves the patients time and effort by avoiding repeat instillation of drops every so often.

In some embodiments, the slow release implant is surgically introduced into subconjunctival space by an ophthalmic surgeon after s/he has decided that the patient would benefit from the implant following provocative testing using the topical drops. The constituents passively reach the iris and interact with the muscle fibers of the iris changing the size of the pupil. This action leads to an increase in depth of field and improvement in the distance and near vision as noted in this disclosure (see Example 1).

In some embodiments, the implant may be introduced to a subject through surgical intervention, wherein the subject
a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, the implant is useful for correcting presbyopia in a subject. In some embodiments, the implant is useful for reducing the size of pupil in a subject. In some embodiments, the implant is useful for inducing miosis in a subject. In some embodiments, the implant is useful for increasing the depth of field in a subject's eye. In some embodiments, the implant is useful for decreasing the magnitude of higher order aberrations in a subject's eye. In some embodiments, the implant is useful for improving uncorrected near and distance visual acuity in a subject.

Some embodiments relate to a kit comprising an ophthalmic pharmaceutical composition according this disclosure. The kits may include: a) a container (e.g., a syringe, tube, vial, dropper) comprising an ophthalmic pharmaceutical composition as described herein; and b) instructions for use, which may include diagrams, drawings, or photographs, in addition to text. The instructions may include steps of how to handle the material (which may include storage conditions, such as temperature ranges for storage), how often to apply the composition, and what to expect from using the composition.

In some embodiments, the kit may be provided to a subject, wherein the subject
a) is a spectacle wearer who cannot or will not use progressive or bifocal lenses;
b) underwent cataract surgery;
c) developed presbyopia after a corneal procedure;
d) has mono-focal or multifocal intraocular lenses;
e) uses contact lenses and does not tolerate mono-vision contact lenses;
f) uses contact lenses and does not tolerate multifocal contact lenses;
g) suffers from a higher order aberration after corneal surgery;
h) suffers from hyperopia or tropias;
i) does not tolerate a change in spectacle prescription;
j) experiences a rapid change in spectacle prescription;
k) is at risk of falls when using progressive or bifocal lenses; and/or
l) suffers from a higher order aberration at night or under dull light conditions.

In some embodiments, the kit is useful for correcting presbyopia in a subject. In some embodiments, the kit is useful for reducing the size of pupil in a subject. In some embodiments, the kit is useful for inducing miosis in a subject. In some embodiments, the kit is useful for increasing the depth of field in a subject's eye. In some embodiments, the kit is useful for decreasing the magnitude of higher order aberrations in a subject's eye. In some embodiments, the kit is useful for improving uncorrected near and distance visual acuity in a subject.

Measures for Assessing Improvement in Presbyopia

One of the effects of changes in pupil size is an alteration of the depth of field (DoF) and visual acuity. The depth of field of the eye is defined as the distance in dioptres a viewed object can be moved towards or away from the eye until the retinal image is judged no longer reasonably clear by the subject whilst the eye remains in a fixed refractive state (Atchison & Smith, 2000, Optics of the human eye, Edinburgh UK, Butterworths-Heinemann, p. 217). The measured depth of field (DoF) is dependent on several factors including pupil size, visual acuity and the ambient test conditions. The key factors associated with DoF were extensively reviewed by Wang & Ciufredda (2006, Sury Ophthalmol 51:75-85) and later by Pallikaris et al (2011, J Ophthalmol 284961, doi: 10.1155/2011/284961).

Atchison et al (1997, Optom Vis Sci. 74:511-520) used apertures to simulate various pupil sizes and found the mean DoF to increase from 0.59D to 0.86D for a pupil size shift from 4 mm to 2 mm. They only found a small increase of 0.27D. Similarly, Sergienko and Tutchenko (2007, Eur J Ophthalmol 17:836-840) reported a 0.26D increase in DoF corresponding with a 2 mm change of artificial pupil size from 5 mm to 3 mm when the visual acuity was 1.5. Marcos et al (1999, Vision Res. 39:2039-2049) had reported the DoF was also affected by the spectral composition of the observed optotype in association with the changes in artificial pupil size but, the changes were small averaging at just 0.16D. The small change in DoF when the pupil size reduces by about 50% is unremarkable. However, these results were obtained on relatively small groups of trained subjects with high visual acuity. Others have observed, with central fixation the DoF can be as high as ±2.5D with a tendency to increase in older subjects (Ronchi & Moleskini, 1975, Ophthalmic Res 7:152-157). The increase is probably associated with naturally occurring age related miosis and change in contrast sensitivity. Mordi and Ciufredda (1998, Vision Res. 38:1643-1653) predicted DoF to rise by 0.027D/annum between 21 and 50 years of age. This is equivalent to 0.80D increase over 30 years. The growing body of evidence clearly points to the conclusion: reducing pupil size will increase the DoF. Tabanero and Artal (2012, J Cataract Refract Surg 38:270-277) elegantly demonstrated DoF can be raised by upto 2.5D when the 1.6 mm diameter aperture of the Acufocus Kamra corneal implant is correctly positioned simulating an artificial pupil. This artificial pupil, albeit placed close to the actual pupil, is still about 3 to 4 mm away from the true position of the pupil. Studies investigating the effect of pupil size on DoF either used various artificial pupils placed before the eye or measured pupil size directly. The true effect of changes in pupil size on DoF requires paralysis of accommodation, to prevent the effect of the accommodative stimulus on DoF from influencing the actual DoF-pupil size relationship, and placing artificial apertures of various sizes to simulate changes in pupil size when the real pupil is dilated (Mordi & Ciuffreda, 1998, Vision Res. 38:1643-1653). It would be useful to have an update of DoF in real eyes under clinical conditions without paralysis. And, compare pharmacologically induced real changes in actual pupil size with any changes in subjective measures of DoF under normal clinical conditions in normal untrained patients. Miotics, by the biochemical nature, are likely to act not just on the iridic receptors but also those located in at the ciliary body leading to changes in accommodative state and refraction. Thus, a miotic is required that promotes sufficient constriction of the pupil with next to no effect on the optical power of the crystalline lens.

Procedure for Estimating Depth of Field (DoF) at Distance

DoF can be estimated after constructing a defocus curve (Toto et al., 2007, J Cataract Refract Surg 33:1419-1425; Gupta et al., 2007, Cont Lenses Anterior Eye 30:119-124; Cillino et al., 2008, Ophthalmology 115:1508-1516; Cleary et al., 2010, J Cataract Refract Surg 36:762-770). The defocus curve is a graphical plot of the measured visual acuities (y axis) associated with the power of a range of trial spherical lenses placed before the eye. This is a stimulus-response curve that can be derived using a variety of psycho-physical techniques. In a clinical setting obtaining data to construct the defocus curve is both time consuming and prone to several sources of error including patient loss of concentration.

A simpler, more rapid, long established technique used by many of the investigators reviewed by Wang and Ciuffreda (2006, Sury Ophthalmol 51:75-85) was used in this study (see Example 1). A modification of the basic technique has also been used in more recent investigations (Yao et al., 2010, Vision Res 50:1266-1273; Bénard et al., 2011, Vision Res 51:2471-2477). The patient was asked to look at the 20/30 line of Snellen optotypes through the best corrected distance spectacle prescription. Plus sphere was increased in the refractor head in 0.25D steps until the patient reported the optotypes were no longer acceptably clear. This was performed on a monocular basis under routine ambient light conditions. Bénard et al (2011, Vision Res 51:2471-2477) determined subjective DoF using 20/50 high contrast letters. Yao et al (2010, Vision Res 50:1266-73) employed high contrast square wave gratings incorporated within a Badal lens set up. The two groups of researchers used different set ups but, the DoF results they found were very similar.

All of the claims in the claim listing are herein incorporated by reference into the specification in their entireties as additional embodiments.

EXAMPLES

Example 1

Improving Unaided Distance and Near Visual Acuity and Depth of Field in Presbyopic and Pseudophakic Eyes by Pharmacological Change in Actual Pupil Size with Pilocarpine Compositions The aim of this example is to measure the effect of actual changes in pupil size on the depth of field (DoF) and visual acuity in presbyopes and monofocal or multifocal IOL implanted pseudophakes attending for routine eye examinations in a clinical setting. Reduction of pupil size increases the DoF and this in turn improves the visual acuity.

Procedure and Vehicle for Reducing Pupil Size (Miosis)

Use of pilocarpine carries the risk of irritation and inflammation following topical instillation.

Mixing an NSAID and tear comfort agent with pilocarpine should act as a preventative measure to combat the inflammatory response and dry eye triggered by the pilocarpine.

As described below, it was found that mixing 0.2% pilocarpine hydrochloride or pilocarpine nitrate with 0.006% diclofenac sodium was well tolerated on topical application and resulted in noticeable miosis. There was no evidence of short or long term undesirable complications associated specifically with topical application of 0.006% diclofenac mixed with sodium hyaluronate of concentration typically associated with tear comfort agents. Therefore, it was decided to prepare a mixture of 0.1% sodium hyaluronate, 0.2% pilocarpine hydrochloride or pilocarpine nitrate, and 0.006% diclofenac sodium for the sole purpose of providing miosis with minimal discomfort. In this example, the percentile numbers are determined by weight (w/v). This combination was issued on a magistral basis to induce miosis during the planned study. The results show that, following topical application of the preparation, the unaided distance and near visual acuities improve with reducing the size of the natural pupil.

Methods and Materials

1. Measurement of Pupil Size

The infrared imaging system used for checking alignment during auto-refractometry was used to measure the pupil size. The infrared image of the pupil converted to visible light, magnified and displayed on the instrument's viewing screen allows the user to observe the pupil and align the instrument during normal use. The vertical and horizontal pupil diameters were measured on screen with a ruler as the subject glanced at the infinity target. The average of the two measurements was recorded and corrected for magnification (approximately ×7 to ×8) for both vertical and horizontal meridia.

2. Measurement of Visual Acuity

All acuity measurements were taken using a standard Snellen chart at distance and Jaeger charts at near. All values were converted to decimal notation using Halliday's conversion chart.

3. Procedure for Estimating Depth of Field (DoF) at Distance

The patient was asked to look at the 20/30 line of Snellen optotypes through the best corrected distance spectacle prescription. Plus sphere was increased in the refractor head in 0.25D steps until the patient reports blur (+a dioptres). The procedure was repeated using negative lenses (−b dioptres). The DoF at distance=(a+b) dioptres. This was performed on a monocular basis under routine ambient light conditions (350 lux) in both presbyopic and pseudophakic groups.

4. Procedure for Estimating Depth of Field (DoF) at Near

The best corrected distance spectacle prescription was increased by the addition of +2.50D in the refractor head and patient was asked to look at a line of J2 print at 0.40 m. Plus power in the refractor head was increased in 0.25 D steps until patient reports blur (+x dioptres). The procedure was repeated using negative lenses (−y dioptres). The DoF at near=(x+y) dioptres. This was performed on a monocular basis under routine ambient light conditions (350 lux) in the presbyopes.

5. Study Design

The investigation was a prospective consecutive nonrandomized interventional study that followed the tenets of the Declaration of Helsinki. All presbyopic subjects were recruited from patients attending for routine eye examinations. The exclusion criteria included amblyopic eyes, cases with history of ocular disease or surgery, cataract, macular degeneration, irregular pupils, any systemic condition known affect pupil dynamics or quality of vision. The pseudophakic patients were also recruited from those attending for routine eye examinations. The exclusion criteria included amblyopic eyes, cases with history of ocular complications, implanted with toric or multifocal IOLs, signs of macular degeneration, capsular thickening, irregular pupils, any systemic condition known to affect the pupil dynamics or quality of vision. Where appropriate, the measurements were taken from both right and left eyes. All subjects were fully informed of the nature and purpose of this investigation.

Data were harvested before and one hour after topical application of one or two drops per eye of the preparation. Any symptoms noticed by the subjects (such as, dryness, nausea, grittiness) were also recorded.

6. Response Measures and Statistical Analyses

The data were analysed to

1) Determine if uncorrected distance visual acuity was affected by drop instillation in the presbyopes and pseudophakes (Wilcoxon signed rank test);
2) Determine if uncorrected near visual acuity was affected by drop instillation in the presbyopes and pseudophakes (Wilcoxon signed rank test);
3) Compare measures of DoF at distance between presbyopes and pseudophakes (t-test);
4) Determine if there was any association between measured pupil size, age and measures of DoF at distance for the presbyopes and pseudophakes (Pearson correlation coefficient);
5) Determine if there was any association between measured pupil size, age and measures of DOF at near for the presbyopes (Pearson correlation coefficient); and 6) Determine if any changes in DoF at distance was associated with any change in pupil size (Pearson correlation coefficient).

In those cases where measurements were taken from both eyes, where appropriate data from right and left eyes were kept separate to prevent making type 1 statistical errors. The significance level was set at a p value of less than 0.05. The Bonferonni correction was applied because data were subjected to multiple comparisons.

Results

Twenty-seven (27) subjects received 1 drop per eye and eighteen (18) subjects received 2 drops per eye of the ophthalmic pharmaceutical composition. For those subjects who received two drops per eye, the second drop was administered seconds after the first one.

The presbyopic group consisted of 18 females and 11 males. A total of 5 experienced and reported adverse reactions of nausea (n=1), dryness (n=1), a burning sensation (n=1), blurred vision (n=1) and stinging (n=1). The pseudophakic group consisted of 10 females and 6 males. In this group, 2 reported a stinging sensation and another 2 experienced a burning sensation after drop instillation. The reported reactions were short lived and not overtly troublesome.

In both groups, uncorrected visual acuity at both distance and near improved significantly following instillation of the drop having the composition as disclosed in this example. There was a concurrent and significant increase in the mean depth of field and reduction in the size of the pupil. The main results are shown in tables 1 and 2.

TABLE 1

Presbyopes- Depth of field, pupil size and unaided visual acuity.

| Measurement | Before | After | Significance |
|---|---|---|---|
| RIGHT EYES (n = 29) | | | |
| Depth of Field, distance (D) | 1.31 (0.42) | 1.97 (0.61) | <0.001 |
| Pupil Diameter (mm) | 3.89 (0.74) | 3.14 (0.75) | <0.001 |
| Depth of Field, near (D) | 1.64 (0.39) | 2.20 (0.54) | <0.001 |
| UDVA (mean ± sd) | 1.10 (0.32) | 1.33 (0.40) | <0.001 |
| UDVA (median & range) | 1.2 (0.5-1.0) | 1.5 (0.60-2.0) | <0.001 |
| UNVA (mean ± sd) | 0.33 (0.17) | 0.45 (0.27) | <0.001 |
| UDVA (median & range) | 0.25 (0.10-0.63) | 0.40 (0.10-0.80) | <0.001 |
| LEFT EYES (n = 24) | | | |
| Depth of Field, distance (D) | 1.41 (0.45) | 2.02 (0.59) | <0.001 |
| Pupil Diameter (mm) | 3.84 (0.81) | 3.16 (0.76) | <0.001 |
| Depth of Field, near (D) | 1.69 (0.36) | 2.19 (0.52) | <0.001 |
| UDVA (mean ± sd) | 1.09 (0.30) | 1.28 (0.38) | <0.001 |
| UDVA (median & range) | 1.0 (0.50-1.5) | 1.2 (0.60-1.50) | <0.001 |
| UNVA (mean ± sd) | 0.31 (0.19) | 0.46 (0.26) | <0.001 |
| UDVA (median & range) | 0.25 (0.1-0.63) | 0.36 (0.1-0.80) | <0.001 |

TABLE 2

Pseudophakes- Depth of field, pupil size and unaided visual acuity.

| Measurement | Before | After | Significance |
|---|---|---|---|
| RIGHT EYES (n = 13) | | | |
| Depth of Field, distance (D) | 1.61 (0.51) | 2.67 (0.52) | <0.001 |
| Pupil Diameter (mm) | 2.92 (0.36) | 1.97 (0.26) | <0.001 |
| UDVA (mean ± sd) | 0.64 (0.18) | 0.89 (0.16) | <0.001 |
| UDVA (median & range) | 0.70 (0.3-1.0) | 0.90 (0.7-1.2) | <0.001 |
| UNVA (mean ± sd) | 0.30 (0.16) | 0.71 (0.15) | <0.001 |
| UNVA (median & range) | 0.30 (0.1-0.55) | 0.70 (0.5-1.0) | <0.001 |
| LEFT EYES (n = 15) | | | |
| Depth of Field, distance (D) | 1.65 (0.52) | 2.72 (0.47) | <0.001 |
| Pupil Diameter (mm) | 2.97 (0.43) | 1.91 (0.23) | <0.001 |
| UDVA (mean ± sd) | 0.69 (0.16) | 0.91 (0.14) | <0.001 |
| UDVA (median & range) | 0.7 (0.40-1.0) | 0.9 (0.70-1.0) | <0.001 |
| UNVA (mean ± sd) | 0.34 (0.17) | 0.76 (0.13) | <0.001 |
| UNVA (median & range) | 0.40 (0.1-0.55) | 0.80 (0.6-1.0) | <0.001 |

Compared with the pseudophakic group, the mean pupil size was significantly larger in the presbyopic group both before and after drop instillation (p<0.001). There was no significant difference in the mean depth of field between groups before drop instillation. However, the difference between groups was significant following drop instillation (p<0.001) (Tables 1 and 2).

In the presbyopic group, there was no significant association between i) pupil size and age ii) age and depth of field at distance or near iii) pupil size and depth of field at distance or near.

In the pseudophakic group, there was no significant association between i) pupil size and age ii) age and depth of field at distance iii) pupil size and depth of field.

Within each group there was no significant difference between results obtained from right eyes compared with left eyes in binocular cases. As there was no obvious bias towards the right or left eyes, data obtained from right and left eyes could be pooled for specific types of analysis. For example, in FIGS. 1 and 2, when considering the possible association between the change in depth of field ($\Delta$DoF) and change in pupil size ($\Delta$pupil) for individual cases, the data obtained from right and left eyes were pooled for specific types of analysis.

Figure 2:
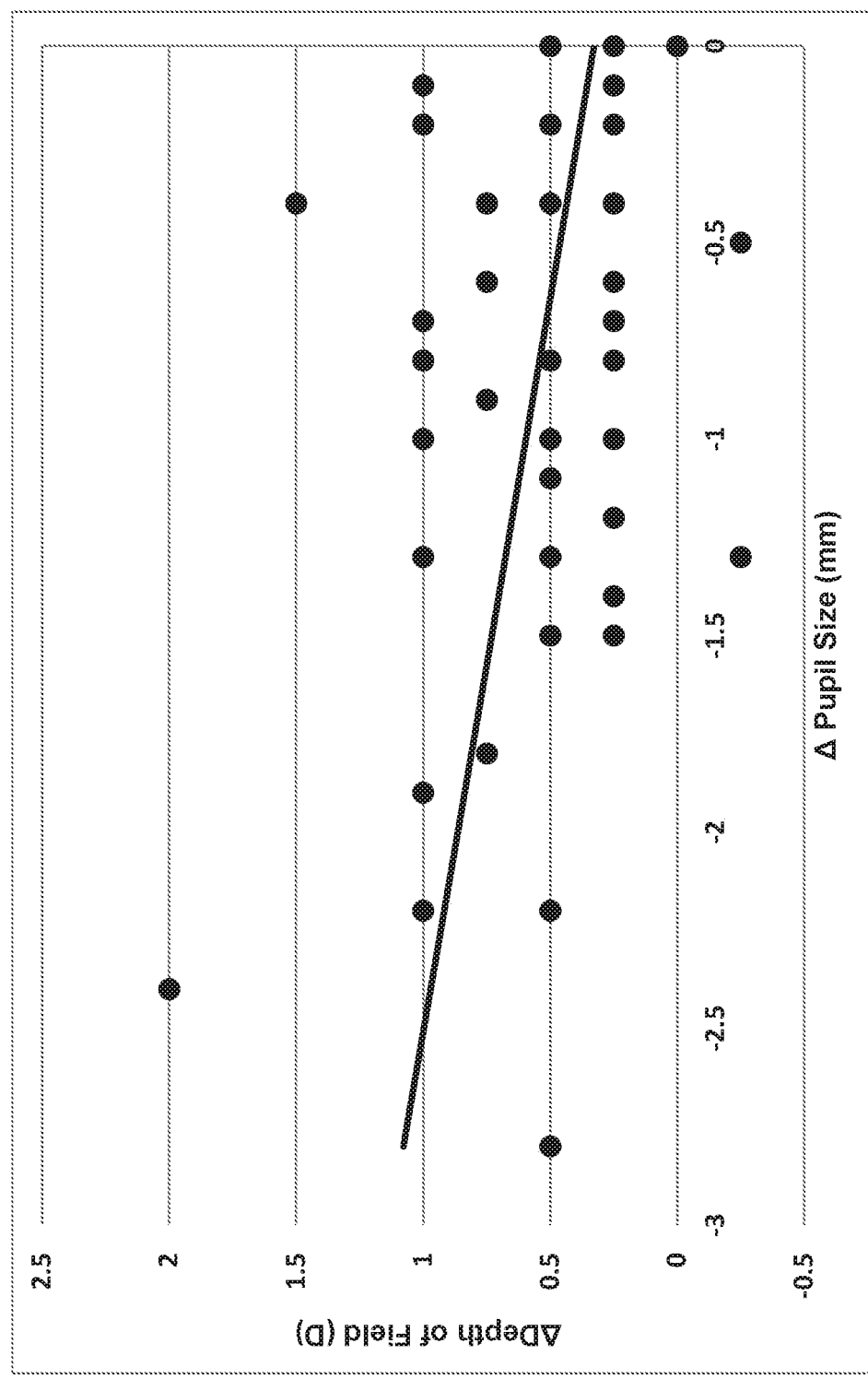
FIG. 2 illustrates the relationship between change in depth of field ($\Delta$DoF) and change in pupil size ($\Delta$pupil) in the presbyopic group (filled circle) looking at a near letters (40 cm) after drop instillation of an ophthalmic pharmaceutical composition according to this disclosure.

In the presbyopic group, there was a significant correlation between $\Delta$DoF and $\Delta$pupil. These results are shown in FIG. 1 (at distance) and FIG. 2 (at near). The least squares regression line equating $\Delta$DoF (y, dioptres) at distance and $\Delta$pupil (x, mm) was of the form:

$$y=0.409-0.289x (r=-0.437, n=53, p<0.001) \quad [\text{eq.1}]$$

Similarly, the least squares regression line equating $\Delta$DoF (y, dioptres) at near and $\Delta$pupil (x, mm) was of the form:

$$y=0.352-0.253x (r=-0.429, n=53, p<0.001) \quad [\text{eq.2}]$$

Within the pseudophakic group, a significant correlation between $\Delta$DoF and $\Delta$pupil was not found. A significant correlation was uncovered after bringing together all the data from both groups. The least squares regression line equating $\Delta$DoF at distance and pupil for the combined data was of the form:

$$y=0.526-0.299x (r=-0.395, n=81, p<0.001) \quad [\text{eq.3}]$$

Discussion

Forty-five subjects participated in this pilot study of which 29 were presbyopes and 16 were pseudophakes (subjects with monofocal IOL implanted). A total of 9 of the 45 subjects (20%) reported a mild sensation after the drop was instilled. One complained of dryness, another noticed a blurring of vision, one felt nausea and headache, three experienced a stinging sensation and another three described this sensation as burning after the drop was instilled. None of the subjects expressed total dissatisfaction after the drops were instilled.

In both groups, the unaided distance and near visual acuity improved following topical application of the preparation. Converting data noted in tables 1 and 2 into Snellen and Jaegar notation show that, in the presbyopes the typical unaided distance acuity improved from 20/20 to 20/15 and the unaided near acuity improved from about J8 to J6. Turning to the results in Table 1, a 0.72 mm fall in pupil size in the presbyopes was associated with this improvement in both unaided distance and near acuity. In the pseudophakic group the typical unaided distance acuity improved from 20/30 to 20/25 and the unaided near acuity improved from J8 to J3. The results in tables 1 and 2 show that in the cohort of pseudophakes a 1.01 mm fall in pupil size was associated with a greater improvement in the unaided near acuity and smaller improvement in the unaided distance acuity when compared with the presbyopes.

This anomaly may be associated with the pupil being smaller in the pseudophakes from the outset. Pupil size tends to be smaller in older subjects compared with the young (Birren et al, 1950, J Gerontol 5: 216-221; Winn et al., 1994, Investigative Ophthalmology & Visual Science 35:1132-1137). There was no correlation between age and pupil size in each of our two groups. However, the mean (±sd) pupil size and age in the presbyopic group was 3.89 mm (0.74, right eyes), 3.84 mm (0.81, left eyes) and 48.7 y (4.20). In the pseudophakic group the corresponding values were 2.92 mm (0.36), 2.97 mm (0.43) and 67.2y (±7.5). The differences between the two groups were significant for both pupil size and age. The smaller pupil in the pseudophakic group was probably related to the age of this cohort of subjects rather than the patients having undergone cataract surgery. This coupled with the difference in optical properties between phakic presbyopic and pseudophakic probably account for the slight difference in response to the drop.

The mean DoF values in both groups prior to drop application were remarkably similar to previous reports. Table 1 shows mean(±sd) DoF values of 1.31D (0.42) and 1.41D (0.45) at distance in the presbyopes. These values fall within the range of upto 1.8D reported in the extensive review on the topic by Wang and Ciuffreda (2006, Sury Ophthalmol 51:75-85). Table 2 shows mean DoF values of 1.61D (0.51) and 1.65D (0.52) at distance in the pseudophakic eyes. These values correspond within the limits of 0.80D to 1.65D reported after implanting monofocal IOLs. (Kamlesh & Kaushik, 2001, Can J Ophthalmol 36:197-201; Macsai et al, 2006, J Cataract Refract Surg. 32:628-633; Nishi et al., 2013, Clin Ophthalmol 7:2159-2164).

In both the presbyopic and pseudophakic groups the mean DoF increased after drop instillation. In the pseudophakic group the mean increase in DoF of 1.03D accompanied a mean decrease in pupil size of 1.05 mm. And, in the presbyopic group the mean increase in DoF of 0.60D accompanied a mean decrease in pupil size of 0.76 mm. The measured depth of field at distance did not change in 5 of the 53 presbyopic eyes. However, in the same 5 cases, the pupil size decreased and the measured depth of field increased at near by upto 1D. Pooling all the data at our disposal revealed a significant association between change in pupil size ($\Delta$pupil) and change in DoF ($\Delta$DoF). The indices of the linear regression equations predict, a 1 mm fall in pupil size should lead to a 0.83D increase in the DoF at distance and a concurrent increase of 0.61D at near.

As noted earlier, the unaided distance and near visual acuity improved following topical application of the preparation.

None of the 45 subjects expressed total dissatisfaction regarding the preparation even though 9 of the subjects reported an adverse reaction. It was well tolerated and subjects requested if the preparation could be supplied to them on a more permanent basis.

Example 2

Safety, Tolerability and Efficacy of CSF-1 in Presbyopia

CSF-1 is a topical ophthalmic drop comprising 0.2% pilocarpine hydrochloride or pilocarpine nitrate, 0.006% diclofenac sodium, 0.1% sodium hyaluronate, and 0.8% hydroxypropyl methylcellulose. In this example, the percentile numbers are determined by weight (w/w). It is designed to provide miosis and increase the depth of field for the temporary correction of presbyopia. The placebo includes the same ingredients as the investigational product, excluding the active ingredients.

Subjects

This example was a double-blind, randomized, placebo-controlled, two-way crossover repeated administration study performed in presbyopic subjects. After signing informed consent and undergoing screening evaluation, eligible subjects were randomized in a 1:1 ratio to one of two treatment sequences as follows:

|   | Treatment Sequence 1 (n = 18) | Treatment Sequence 2 (n = 18) |
|---|---|---|
| 1 | CSF-1 | Placebo |
| 2 | Placebo | CSF-1 |

Each treatment, CSF-1 or placebo, was self-administered by the subject over two weeks (one drop in each eye every morning), with a 24-hour washout interval between treatments. The permitted interval between treatment visits was 11 to 17 days. All subjects, regardless of their treatment arm assignment, underwent the same evaluations. Each subject continued to be followed for two weeks after the end of the treatment period. The maximal duration for an individual patient was 64 days (-9 weeks) including:

Screening period: up to 21 days inclusive;
Treatment period: 29 days; and
Follow-up period: 14 days.

The study objectives were:
1) To establish safety and tolerability of repeated administration of CSF-1 in presbyopic subjects; and
2) To determine the efficacy of repeated administration of CSF-1 in presbyopic subjects.

Methods and Materials 1. Measurement of pupil size

The infrared imaging system used for checking alignment during auto-refractometry was used to measure the pupil size. The infrared image of the pupil converted to visible light, magnified and displayed on the instrument's viewing screen allows the user to observe the pupil and align the instrument during normal use. The vertical and horizontal pupil diameters were automatically measured by the built-in software of the imaging system as the subject glanced at the infinity target. The measurement was recorded and corrected for magnification (approximately ×7 to ×8) for both vertical and horizontal meridia.

2. Measurement of Visual Acuity

All acuity measurements were taken using FDA approved standard EDTRS charts at distance and at near. EDTRS charts provide acuity measurements in Snellen, decimal and logMAR notations. The design of these charts features a simple 0.1 unit progression in letter size on the logMAR scale from one line of letters to the next and, scales for converting to other notations such as Snellen or decimal. For example, when a person can only identify letters on say line 11 which, in the 4M distance ETDRS chart, is designated as 20/20 Snellen acuity, then her/his acuity could be noted as either 0.0 logMAR or 1.0 decimal besides 20/20. An ability to identify letters on the next line, which is line 12, would indicate an acuity of −0.1 logMAR or 1.25 decimal or 20/16 Snellen. The logMAR notification is more sensitive and provides valid statistical comparisons. Distance acuity was measured at each eye both monocularly (right eye followed by left eye) and binocularly under standard high ambient illumination (~3,000 Lux) for acuity checking. Near acuity was measured at 40 cm at each eye both monocularly (right eye followed by left eye) and binocularly under standard high (~3,000 Lux) ambient illumination and repeated under lower (20-1,000 Lux) illumination.

3. Procedure for Estimating Peripheral Visual Fields

The visual fields were assessed using a standard clinical procedure commonly referred to as the confrontation test known in the art. This test checks for any loss or anomaly in the upper, lower, nasal and temporal regions of the visual field of each eye.

4. Procedure for Estimating Depth of Field (DoF) at Distance

The patient was asked to look at the 0.1 logMAR line of optotypes through the best corrected distance spectacle prescription. Plus sphere was increased in the refractor head in 0.25D steps until the patient reports blur (+a dioptres). The procedure was repeated using negative lenses (−b dioptres). The DoF at distance =(a+b) dioptres. This was performed on a monocular basis under routine ambient light conditions (~3000 lux).

5. Procedure for Estimating Depth of Field (DoF) at Near

The patient was asked to look at the 0.1 logMAR line of optotypes through the best corrected distance spectacle prescription. Plus sphere was increased in the refractor head in 0.25D steps until the patient reports blur (+a dioptres).

The procedure was repeated using negative lenses (−b dioptres). The DoF at distance=(a+b) dioptres. This was performed on a monocular basis under routine ambient light conditions (3000 lux).

6. Procedure for Estimating Efficacy

The primary efficacy end-point was defined as either 0.2 or 0.3 improvement in the unaided near (UNVA) visual acuity according to the logMAR notation. This was equivalent to either 2 or 3 lines of improvement in the acuity using the standard EDTRS chart for near vision (40 cm).

7. Study Design

The study was a double-masked, twin-centre, randomized, placebo-controlled, repeated administration, crossover study to establish the safety, tolerability and efficacy of CSF-1 in presbyopic that followed the tenets of the Declaration of Helsinki. All presbyopic subjects were recruited from patients attending for routine eye examinations. All subjects had best corrected visual acuity of at least 20/20 equivalent to 0.0 on logMAR scale and all were dependent on reading glasses or bifocals in which the near addition is >+1.00 Dioptres. In addition, all subjects required either no distance optical correction or a low distance correction where the spherical component was no greater than ±0.75 Dioptres and/or the cylindrical component was no greater than ±0.75 DC, refraction along any principal meridian no greater than 1.00 Dioptres. The exclusion criteria included amblyopic eyes, cases with anomalies relating to binocular vision, oculo-motor dysfunction, history of ocular disease or surgery, cataract, macular degeneration, irregular pupils, natural pupil size less than 2.5 mm in either eye at ambient light of 8-15 lux, and any systemic condition known affect pupil dynamics or quality of vision. Where appropriate, the measurements were taken from both right and left eyes. All subjects were fully informed of the nature and purpose of this investigation.

Data were collected before and at later visits to the clinic after the subject had been self-administering the topical application (CSF-1 or the placebo) to both eyes of the preparation on a daily basis. Any symptoms noticed by the subjects (such as dryness, nausea, and grittiness) were also recorded.

8. Response Measures and Statistical Analyses

The data were analysed to 1) Determine if uncorrected distance visual acuity was affected by the drops;
2) Determine if uncorrected near visual acuity was affected by the drops;
3) Determine if pupil size was affected by the drops; and
4) Determine if depth of field at distance and near was affected by the drops.

Appropriate statistical tests such as McNemar's test for matched pairs and paired t-test or signed-rank test for two means (paired observations) were applied for analyzing the quantitative changes. All tests were two-tailed, and a p-value of 5% or less was considered statistically significant.

Results

Thirty-six subjects (21 females and 15 males, mean age 51.5 [sd=±4.43], range 44.5 to 62.5 years) completed the study.

In both eyes and in right eye, there was no overall difference between CSF-1 and the placebo on the uncorrected distance visual acuity. In the left eye, CSF-1 significantly improved uncorrected visual acuity. The difference between CSF-1 and the placebo in the left eye was statistically significant. The key information was featured in Table 3.

TABLE 3

Uncorrected distance (4 m) visual acuity - frequency of changes at standard high illumination. BV = with both eyes; OD = right eye; and OS = left eye.

|   | Change from Baseline | N | % | P-value (Signed-rank test)* |
|---|---|---|---|---|
|   | Change with CSF-1 |   |   |   |
| BV | −1 | 3 | 8.3 |   |
|   | 0 | 19 | 52.8 |   |
|   | 1 | 11 | 30.6 |   |
|   | 2 | 3 | 8.3 |   |
|   | Change with Placebo |   |   |   |
|   | −1 | 5 | 13.9 |   |
|   | 0 | 24 | 66.7 | 0.0933 |
|   | 1 | 6 | 16.7 |   |
|   | 2 | 1 | 2.8 |   |
|   | Change with CSF-1 |   |   |   |
| OD | −2 | 1 | 2.8 |   |
|   | −1 | 5 | 13.9 |   |
|   | 0 | 11 | 30.6 |   |
|   | 1 | 14 | 38.9 |   |
|   | 2 | 4 | 11.1 |   |
|   | 3 | 1 | 2.8 |   |
|   | Change with Placebo |   |   |   |
|   | −1 | 5 | 13.9 |   |
|   | 0 | 19 | 52.8 |   |
|   | 1 | 9 | 25.0 | 0.2295 |
|   | 2 | 3 | 8.3 |   |
|   | Change with CSF-1 |   |   |   |
| OS | −2 | 1 | 2.8 |   |
|   | −1 | 2 | 5.6 |   |
|   | 0 | 14 | 38.9 |   |
|   | 1 | 11 | 30.6 |   |
|   | 2 | 6 | 16.7 |   |
|   | 3 | 2 | 5.6 |   |
|   | Change with Placebo |   |   |   |
|   | −1 | 7 | 19.4 |   |
|   | 0 | 17 | 47.2 |   |
|   | 1 | 9 | 25.0 | 0.0008 |
|   | 2 | 3 | 8.3 |   |

*P-value obtained from Signed-rank test indicates the statistical significance of the difference between changes at CSF-1 and at the placebo.

There was a significant change in the mean uncorrected near visual acuity after using CSF-1 compared with any change after using the placebo. The change following CSF-1 treatment was substantially greater than any change found using the placebo. The key information was featured in Tables 4-6.

TABLE 4

Uncorrected near visual acuity (high illumination). Success was defined as at least 2 or 3 lines improvement from baseline according to the ETDRS chart.

|   |   | CSF-1 | | Placebo | | P-value |
|---|---|---|---|---|---|---|
|   | Success Rate | N | % | N | % | McNemar's Test |
| BV | Success by 2 lines |   |   |   |   |   |
|   | Failure (<2) | 21 | 58.3 | 28 | 77.8 |   |
|   | Success (≥2) | 15 | 41.7 | 8 | 22.2 | 0.0348 |
|   | Success by 3 lines |   |   |   |   |   |
|   | Failure (<3) | 27 | 75.0 | 34 | 94.4 |   |
|   | Success (≥3) | 9 | 25.0 | 2 | 5.6 | 0.0196 |

TABLE 4-continued

Uncorrected near visual acuity (high illumination).
Success was defined as at least 2 or 3 lines improvement
from baseline according to the ETDRS chart.

|    | Success Rate      | CSF-1 N | CSF-1 % | Placebo N | Placebo % | P-value McNemar's Test |
|----|-------------------|---------|---------|-----------|-----------|------------------------|
| OD | Success by 2 lines |         |         |           |           |                        |
|    | Failure (<2)      | 20      | 55.6    | 28        | 77.8      |                        |
|    | Success (≥2)      | 16      | 44.4    | 8         | 22.2      | 0.0455                 |
|    | Success by 3 lines |         |         |           |           |                        |
|    | Failure (<3)      | 27      | 75.0    | 31        | 86.1      |                        |
|    | Success (≥3)      | 9       | 25.0    | 5         | 13.9      | 0.2059                 |
| OS | Success by 2 lines |         |         |           |           |                        |
|    | Failure (<2)      | 24      | 66.7    | 31        | 86.1      |                        |
|    | Success (≥2)      | 12      | 33.3    | 5         | 13.9      | 0.0707                 |
|    | Success by 3 lines |         |         |           |           |                        |
|    | Failure (<3)      | 31      | 86.1    | 35        | 97.2      |                        |
|    | Success (≥3)      | 5       | 13.9    | 1         | 2.8       | 0.0455                 |

BV = with both eyes; OD = right eye; and OS = left eye.

TABLE 5

Uncorrected near visual acuity (low illumination).
Success was defined as at least 2 or 3 lines improvement
from baseline according to the ETDRS chart.

|    | Success Rate      | CSF-1 N | CSF-1 % | Placebo N | Placebo % | P-value McNemar's Test |
|----|-------------------|---------|---------|-----------|-----------|------------------------|
| BV | Success by 2 lines |         |         |           |           |                        |
|    | Failure (<2)      | 21      | 58.3    | 30        | 83.3      |                        |
|    | Success (≥2)      | 15      | 41.7    | 6         | 16.7      | 0.0067                 |
|    | Success by 3 lines |         |         |           |           |                        |
|    | Failure (<3)      | 30      | 83.3    | 34        | 94.4      |                        |
|    | Success (≥3)      | 6       | 16.7    | 2         | 5.6       | 0.1025                 |
| OD | Success by 2 lines |         |         |           |           |                        |
|    | Failure (<2)      | 22      | 61.1    | 30        | 83.3      |                        |
|    | Success (≥2)      | 14      | 38.9    | 6         | 16.7      | 0.0209                 |
|    | Success by 3 lines |         |         |           |           |                        |
|    | Failure (<3)      | 28      | 77.8    | 34        | 94.4      |                        |
|    | Success (≥3)      | 8       | 22.2    | 2         | 5.6       | 0.0143                 |
| OS | Success by 2 lines |         |         |           |           |                        |
|    | Failure (<2)      | 20      | 55.6    | 32        | 88.9      |                        |
|    | Success (≥2)      | 16      | 44.4    | 4         | 11.1      | 0.0005                 |
|    | Success by 3 lines |         |         |           |           |                        |
|    | Failure (<3)      | 26      | 72.2    | 35        | 97.2      |                        |
|    | Success (≥3)      | 10      | 27.8    | 1         | 2.8       | 0.0027                 |

BV = with both eyes; OD = right eye; and OS = left eye.

TABLE 6

Uncorrected near visual acuity (either high or low illumination,
left, right or both eyes). Success was defined as at least 2
or 3 lines improvement from baseline according to the ETDRS chart
at either high or low illumination in left, right or both eyes.
BV = with both eyes; OD = right eye; and OS = left eye.

| Success Rate       | CSF-1 N | CSF-1 % | Placebo N | Placebo % | P-value McNemar's Test |
|--------------------|---------|---------|-----------|-----------|------------------------|
| Success by 2 lines |         |         |           |           |                        |
| Failure (<2)       | 11      | 30.6    | 20        | 55.6      |                        |
| Success (≥2)       | 25      | 69.4    | 16        | 44.4      | 0.0290                 |
| Success by 3 lines |         |         |           |           |                        |
| Failure (<3)       | 19      | 52.8    | 30        | 83.3      |                        |
| Success (≥3)       | 17      | 47.2    | 6         | 16.7      | 0.0045                 |

There was a significant change in the mean pupil size after using CSF-1 compared with any change after using the placebo. The key information was featured in Table 7.

TABLE 7

Changes in pupil size (mm) following use of CSF-1 or the placebo.

| Pupil Size | N | Mean | Std | Min | Median | Max | P-value (Paired T-test) |
|---|---|---|---|---|---|---|---|
| Baseline | 72 | 4.29 | 0.87 | 2.50 | 4.30 | 6.80 | |
| CSF-1 | 72 | 3.10 | 0.93 | 1.60 | 2.95 | 6.00 | |
| Placebo | 70 | 3.67 | 1.13 | 1.50 | 3.95 | 6.00 | |
| Changes following CSF-1 treatment | 72 | −1.18 | 0.92 | −3.40 | −1.10 | 1.40 | |
| Changes following Placebo treatment | 70 | −0.60 | 1.32 | −3.50 | −0.40 | 3.20 | |
| Difference between CSF-1 and Placebo | 70 | 0.54 | 1.51 | −3.50 | 0.80 | 3.20 | 0.0037 |

There was a significant change in the mean depth of field at distance and near after using CSF-1 compared with any change after using the placebo. The key information was featured in Table 8.

TABLE 8

Changes in depth of field (dioptres) following use of CSF-1 or the placebo.

| Depth of Field | N | Mean | Std | Min | Median | Max | P-value (Paired T-test) |
|---|---|---|---|---|---|---|---|
| 40 cm Pre-Treatment | 72 | 3.70 | 2.70 | −5.25 | 4.38 | 8.50 | |
| Changes following CSF-1 treatment | 72 | 0.98 | 2.33 | −5.25 | 0.50 | 12.00 | |
| Changes following Placebo treatment | 70 | 0.57 | 2.33 | −6.50 | 0.25 | 13.00 | |

TABLE 8-continued

Changes in depth of field (dioptres) following use of CSF-1 or the placebo.

| Depth of Field | N | Mean | Std | Min | Median | Max | P-value (Paired T-test) |
|---|---|---|---|---|---|---|---|
| Placebo | 70 | 4.33 | 2.29 | 0.25 | 5.13 | 7.75 | |
| CSF-1 | 72 | 4.68 | 2.57 | 0.25 | 5.00 | 11.00 | |
| Difference between CSF-1 and Placebo | 70 | −0.44 | 1.81 | −9.25 | −0.25 | 5.00 | 0.0462 |
| 4 m Pre-Treatment | 72 | 1.51 | 0.65 | 0.50 | 1.50 | 3.25 | |
| Changes following CSF-1 treatment | 72 | 0.22 | 0.86 | −2.75 | 0.25 | 1.75 | |
| Changes following Placebo treatment | 70 | 0.01 | 0.74 | −2.00 | 0.00 | 2.50 | |
| Placebo | 70 | 1.54 | 0.52 | 0.00 | 1.50 | 3.75 | |
| CSF-1 | 72 | 1.73 | 0.55 | 0.00 | 1.75 | 2.75 | |
| Difference between CSF-1 and Placebo | 70 | −0.21 | 0.65 | −1.50 | −0.25 | 2.25 | 0.0071 |

There was no significant change in the stability of the tear film after using either CSF-1 or the placebo. The key information was featured in Table 9.

TABLE 9

Stability of pre-corneal tear film.

| Tear Film (sec.) and Changes | N | Mean | Std | Min | Median | Max | P-value (Signed-Rank test) |
|---|---|---|---|---|---|---|---|
| OD Baseline | 23 | 13.8 | 3.6 | 9.0 | 14.0 | 20.0 | |
| With CSF-1 | 23 | 14.1 | 5.8 | 5.0 | 14.0 | 28.0 | |
| With Placebo | 23 | 15.0 | 3.6 | 8.0 | 15.0 | 22.0 | |
| At Follow-up | 21 | 14.5 | 4.4 | 6.0 | 15.0 | 25.0 | |
| Changes following CSF-1 treatment | 23 | 0.3 | 6.3 | −12.0 | 0.0 | 15.0 | 0.7753 |
| Changes following Placebo | 23 | 1.2 | 4.6 | −10.0 | 2.0 | 7.0 | 0.1473 |
| OS Baseline | 23 | 13.8 | 3.1 | 9.0 | 14.0 | 22.0 | |
| With CSF-1 | 23 | 14.5 | 6.0 | 3.0 | 15.0 | 30.0 | |
| With Placebo | 23 | 13.9 | 3.8 | 5.0 | 14.0 | 20.0 | |
| At Follow-up | 21 | 14.1 | 4.7 | 4.0 | 15.0 | 25.0 | |
| Changes following CSF-1 treatment | 23 | 0.7 | 6.4 | −11.0 | 0.0 | 14.0 | 0.7880 |
| Changes following Placebo | 23 | 0.1 | 5.2 | −11.0 | 1.0 | 7.0 | 0.8930 |

OD = right eye and OS = left eye.

Discussion

Uncorrected Distance Visual Acuity

Pilocarpine at certain concentrations will stimulate the ciliary muscle resulting in accommodation and reduced distance acuity (see, e.g., Emsley, 1972, Optics of Vision, 5$^{th}$ ed., Visual Optics Vol. 1, London UK, Butterworths, p. 88; Williams, 1976, J Am Optom Assoc 47:761-764; Mazor et al., 1979, Br J Ophthalmol 63:48-51; Edgar et al., 1999, Graefes Arch Clin Exp Ophthalmol 237:117-124). CSF-1 improved uncorrected near vision, but did not reduce uncorrected distance visual acuity. As the distance vision was not impaired (Table 3), the data indicate that no accommodation was triggered by CSF-1. More specifically, an unexpected 91.7% of eyes presented with no change in uncorrected distance visual acuity following treatment with CSF-1. When using the placebo, only 86.2% of eyes presented with no change in uncorrected distance visual acuity.

Uncorrected Near Visual Acuity

Only concentrations of pilocarpine above 0.5% are effective in improving near vision (U.S. Pat. No. 9,579,308). However, the study results showed that binocular unaided near visual acuity at 40 cm unexpectedly improved by 2 or more lines in 41.7% of patients when using CSF-1 and in 22.2% of patients when using the placebo (p=0.0348) under high ambient illumination (Table 4). Under low ambient illumination, 41.7% of patients were unexpectedly recorded as demonstrating such an increase in their binocular uncorrected near visual acuity while only 16.7% were recorded as having such an increase when using the placebo (p=0.0067) (Table 5).

Turning to results taken from individual eyes, under low ambient illumination the uncorrected near visual acuity at 40 cm improved by 3 or more lines in 27.8% of left eyes and 22.2% of right eyes when CSF-1 was administered (Table 5). However, only 2.8% of left eyes and 5.6% right eyes improved by 3 or more lines following use of the placebo (p<0.0143 right eyes & p<0.0027 left eyes) (Table 5). These findings were unexpected because pilocarpine is expected to reduce pupil size, restricting the amount of light entering the eye and this will in turn reduce the brightness of the retinal image and acuity under low ambient light.

Pupil

Low (below 1%) concentration of pilocarpine would have little effect on pupil size (Mazor et al., 1979, Br J Ophthalmol 63:48-51; Edgar et al., 1999, Graefes Arch Clin Exp Ophthalmol 237:117-124). However, the study revealed unexpected and meaningful results of pupil reduction following CSF-1 administration from an average of 4.29 mm before treatment to an average of 3.10 mm following CSF-1 drops (Table 7). Without being bound by any mechanistic theory, the study results suggest that CSF-1 works through pupil reduction, but not accommodation.

Depth of Field

Depth of field has an inverse relationship with pupil size. When the pupil size reduces, the depth of field increases. The depth of field is not expected to change significantly when compared with a placebo when the pupil size does not change. Low (below 1%) concentration of pilocarpine would have little effect on pupil size (Mazor et al., 1979, Br J Ophthalmol 63:48-51; Edgar et al., 1999, Graefes Arch Clin Exp Ophthalmol 237:117-124). Therefore, increase in DoF is not expected to result from the administration of less than 1% pilocarpine. However, the study revealed unexpected and meaningful increases in the depth of field results following CSF-1 administration compared with any changes observed following administration of the placebo at both distance and near (Table 8).

Tear Film

Topical drops containing salts of pilocarpine may induce dry eye resulting from a fall in both tear production and stability of the tear film (Nuzzi et al., 1998, Int Ophthalmol 22:31-35; Baffa et al., 2008, Arq Bras Oftalmol 71:18-21). Unexpectedly, the study did not reveal any meaningful change, either a fall or rise, in the stability of the tear film after use of either CSF-1 or the placebo (Table 9).

Visual Fields Under Conditions of Low Illumination

The pupil miosis produced by pilocarpine has the potential to affect the visual fields and acuity when the ambient light level is reduced. Thus, one would expect to discover some loss of visual field and reduced ability to perform vital tasks where good vision is required at night. Unexpectedly, there were no reports of any loss or reduction in the overall size of the visual fields when the patients were using either CSF-1 or the placebo. The results showed that all 23 patients that were tested for visual field showed normal and no reduction in visual field—both at the drug arm and at the placebo arm. At the commencement of the study 75% of the subjects reported they could drive at night without glasses. This percentage increased to 83% and 86% following use of CSF-1 or the placebo respectively.

What is claimed is:

1. A method of correcting presbyopia in a subject comprising administering to the subject a therapeutically effective amount of an ophthalmic pharmaceutical composition consisting of pilocarpine hydrochloride at a concentration of about 0.4% (w/w or w/v), sodium hyaluronate at a concentration of about 0.1% (w/w or w/v), hydroxypropyl methylcellulose at a concentration of about 0.8% (w/w or w/v), and one or more pharmaceutically acceptable carriers and/or excipients, including one or more stabilizers, sodium chloride, pH agent, and water, wherein the correction of presbyopia occurs via a change in pupil size.

2. The method of claim 1, wherein the one or more stabilizers are selected from the group consisting of sodium hydrogen sulphite and/or ethylenediaminetetraacetic acids, or mixtures thereof.

3. The method of claim 1, wherein the ophthalmic pharmaceutical composition is effective for up to 24 hours and/or effective without adversely affecting night vision.

4. The method of claim 1, wherein the administration is topical or by surgical intervention.

5. The method of claim 1, wherein the subject:
 a) is a spectacle wearer who cannot or will not use progressive or bifocal lenses;
 b) underwent cataract surgery;
 c) developed presbyopia after a corneal procedure;
 d) has mono-focal or multifocal intraocular lenses;
 e) uses contact lenses and does not tolerate mono-vision contact lenses;
 f) uses contact lenses and does not tolerate multifocal contact lenses;
 g) suffers from a higher order aberration after corneal surgery;
 h) suffers from hyperopia or tropias;
 i) does not tolerate a change in spectacle prescription;
 j) experiences a rapid change in spectacle prescription;
 k) is at risk of falls when using progressive or bifocal lenses; and/or
 l) suffers from a higher order aberration at night or under light conditions.

6. The method of claim 1, wherein the ophthalmic pharmaceutical composition is a slow release composition.

7. The method of claim 1, wherein the ophthalmic pharmaceutical composition is in the form of a suspension, gel, ointment, injectable solution, spray, or eye drop formulation.

8. The method of claim 7, wherein the ophthalmic pharmaceutical composition is an eye drop formulation.

9. The method of claim 1, wherein the ophthalmic pharmaceutical composition is suitable for topical delivery to a subject's eye or tissue surrounding the eye.

10. The method of claim 1, wherein the ophthalmic pharmaceutical composition corrects presbyopia without adversely reducing visual field.

11. The method of claim 3, wherein the ophthalmic pharmaceutical composition is effective for up to 12 hours.

12. The method of claim 11, wherein the ophthalmic pharmaceutical composition is effective for up to 8 hours.

* * * * *

UNITED STATES PATENT AND TRADEMARK OFFICE
CERTIFICATE OF CORRECTION

PATENT NO. : 11,129,812 B2
APPLICATION NO. : 16/831535
DATED : September 28, 2021
INVENTOR(S) : Claes Feinbaum, Franc Salamun and Sudhir Patel It is certified that error appears in the above-identified patent and that said Letters Patent is hereby corrected as shown below:

In the Claims

Claim 12, Column 68, Line 37, "the method of claim 11" should read --the method of claim 3--.

Signed and Sealed this
Thirteenth Day of August, 2024

Katherine Kelly Vidal
*Director of the United States Patent and Trademark Office*